US008613905B2

(12) United States Patent
El-Agnaf

(10) Patent No.: US 8,613,905 B2
(45) Date of Patent: Dec. 24, 2013

(54) DIAGNOSTIC AGENT

(75) Inventor: Omar El-Agnaf, Morecombe (GB)

(73) Assignee: United Arab Emirates University, Al Ain Abu Dhabi (AE)

( * ) Notice: Subject to any disclaimer, the term of this patent is extended or adjusted under 35 U.S.C. 154(b) by 391 days.

(21) Appl. No.: 12/675,756

(22) PCT Filed: Aug. 29, 2008

(86) PCT No.: PCT/GB2008/002932
§ 371 (c)(1),
(2), (4) Date: Jul. 16, 2010

(87) PCT Pub. No.: WO2009/027690
PCT Pub. Date: Mar. 5, 2009

(65) Prior Publication Data
US 2010/0284934 A1 Nov. 11, 2010

(30) Foreign Application Priority Data

Aug. 30, 2007 (GB) .................................. 0716885.9

(51) Int. Cl.
A61K 51/00 (2006.01)
A61M 36/14 (2006.01)
(52) U.S. Cl.
USPC ............ 424/1.69; 424/1.11; 424/1.65; 514/1; 514/1.1; 530/300; 530/329; 530/330; 530/331
(58) Field of Classification Search
USPC ............ 424/1.11, 1.65, 1.69, 9.1; 514/1, 1.1; 530/300, 330, 331, 329; 534/7, 10–16
See application file for complete search history.

(56) References Cited

U.S. PATENT DOCUMENTS 5,686,410 A * 11/1997 Albert et al. ................. 424/1.69
7,060,671 B1 * 6/2006 Stott ............................ 424/1.69

FOREIGN PATENT DOCUMENTS

| JP | A-2003-503312 A | 11/2000 |
|----|----|----|
| WO | WO 99/50300 A1 | 10/1999 |
| WO | WO 00/68263 A2 | 11/2000 |
| WO | WO 03/069332 A2 | 8/2003 |
| WO | WO 03/069332 A3 | 8/2003 |
| WO | WO2004/009625 * | 1/2004 |
| WO | WO 2004/009625 A2 | 1/2004 |
| WO | WO 2004/009625 A3 | 1/2004 |
| WO | WO 2007/129077 A2 | 11/2007 |
| WO | WO 2007/129077 A3 | 11/2007 |
| WO | WO 2008/003943 A2 | 1/2008 |
| WO | WO 2008/003943 A3 | 1/2008 |

OTHER PUBLICATIONS

El-Agnaf et al (FASEB, 2004, vol. 18, pp. 1315-1317).*
Amer, D.A.M. et al., "Inhibitors of α-synuclein oligornerization and toxicity: a future therapeutic strategy for Parkinson's disease and related disorders," Exp. Brain Res., 2006, vol. 173, pp. 223-233.
El-Agnaf, O.M.A. et al., "A strategy for designing inhibitors of α-synuclein aggregation and toxicity as a novel treatment for Parkinson's disease and related disorders," The FASEB Journal, Aug. 2004, vol. 18, pp. 1315-1317.
El-Agnaf, O.M.A. et al., "Detection of oligomeric forms of α-synuclein protein in human plasma as a potential biomarker for Parkinson's disease," The FASEB Journal, Mar. 2006, vol. 20, pp. 419-425.
International Search Report mailed on Jan. 29, 2009, for International Application No. PCT/GB2008/002932 filed on Aug. 29, 2008, 5 pages.

* cited by examiner

Primary Examiner — D L Jones
(74) Attorney, Agent, or Firm — Kilpatrick Townsend & Stockton LLP

(57) ABSTRACT

The invention provides an agent comprising an amino acid sequence for use in a method of diagnosis of a synucleinopathic disease.

6 Claims, 22 Drawing Sheets

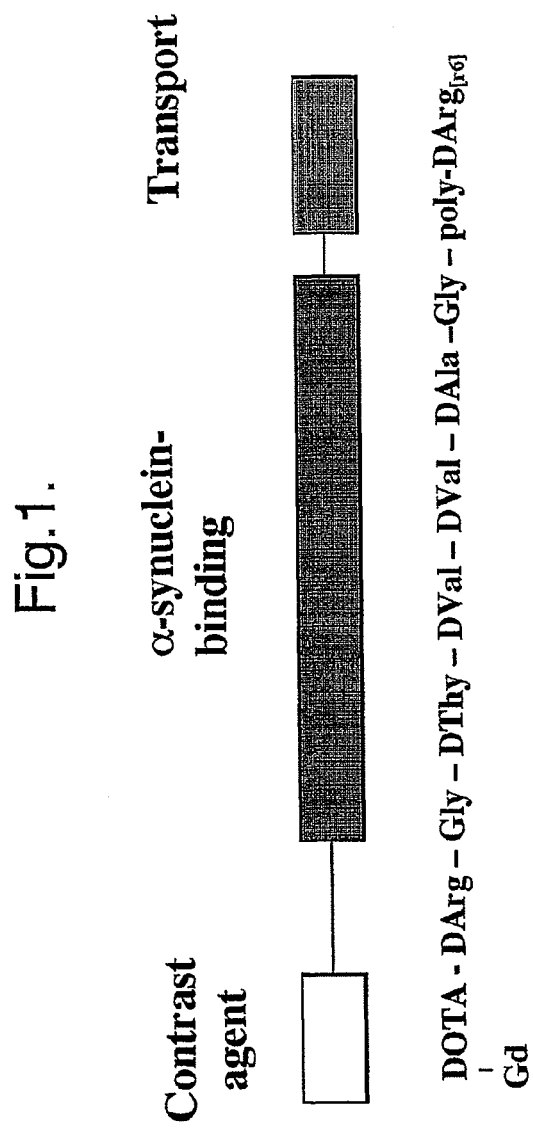

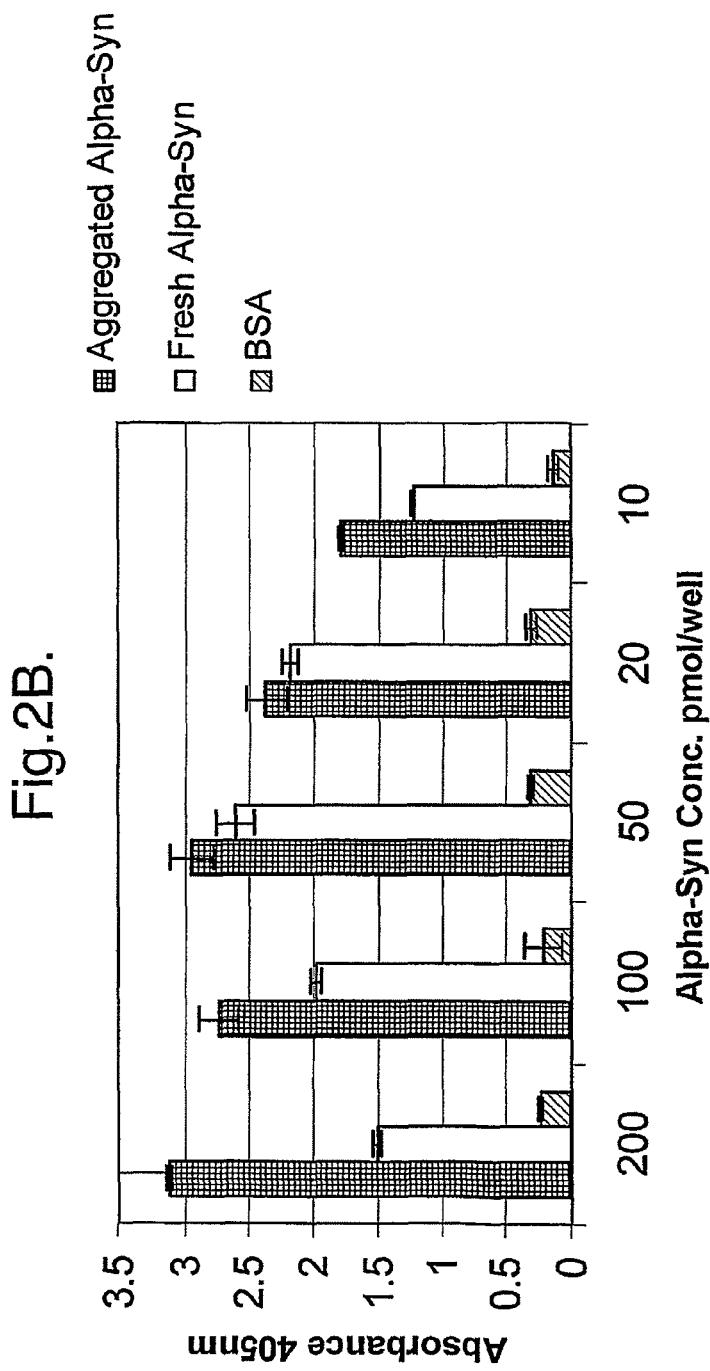

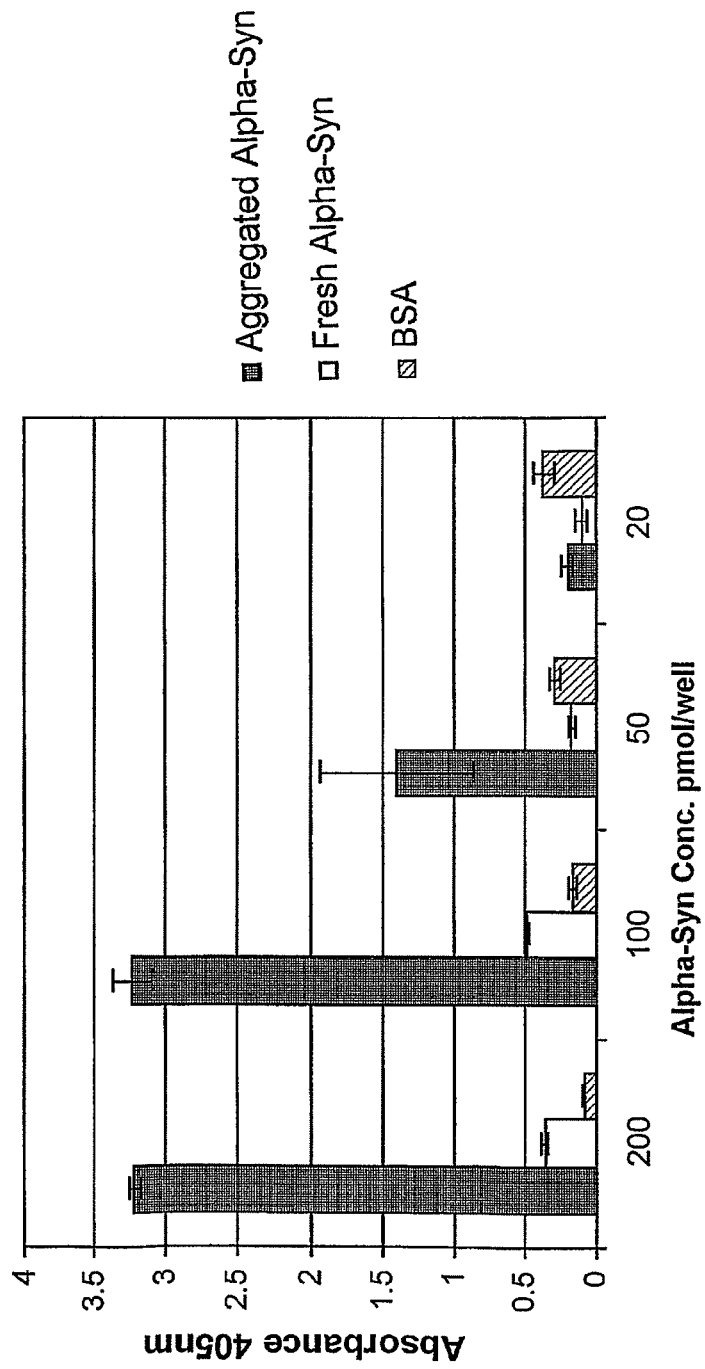

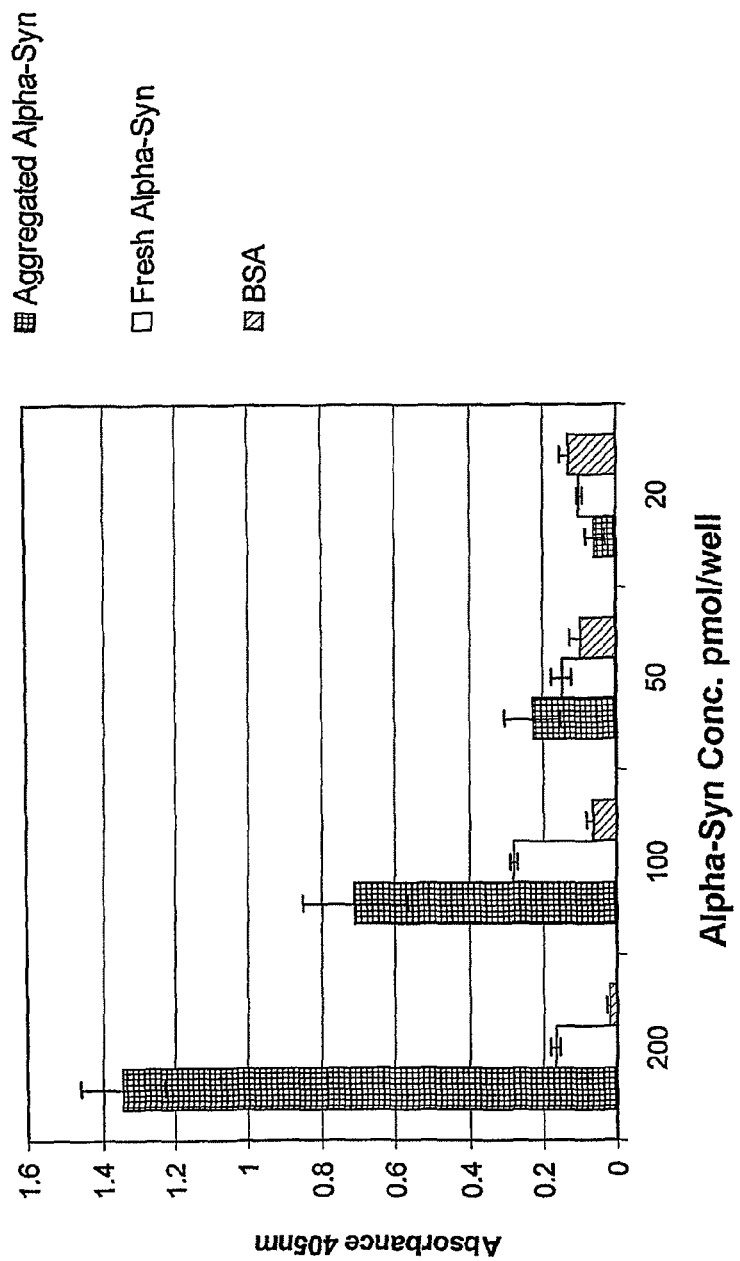

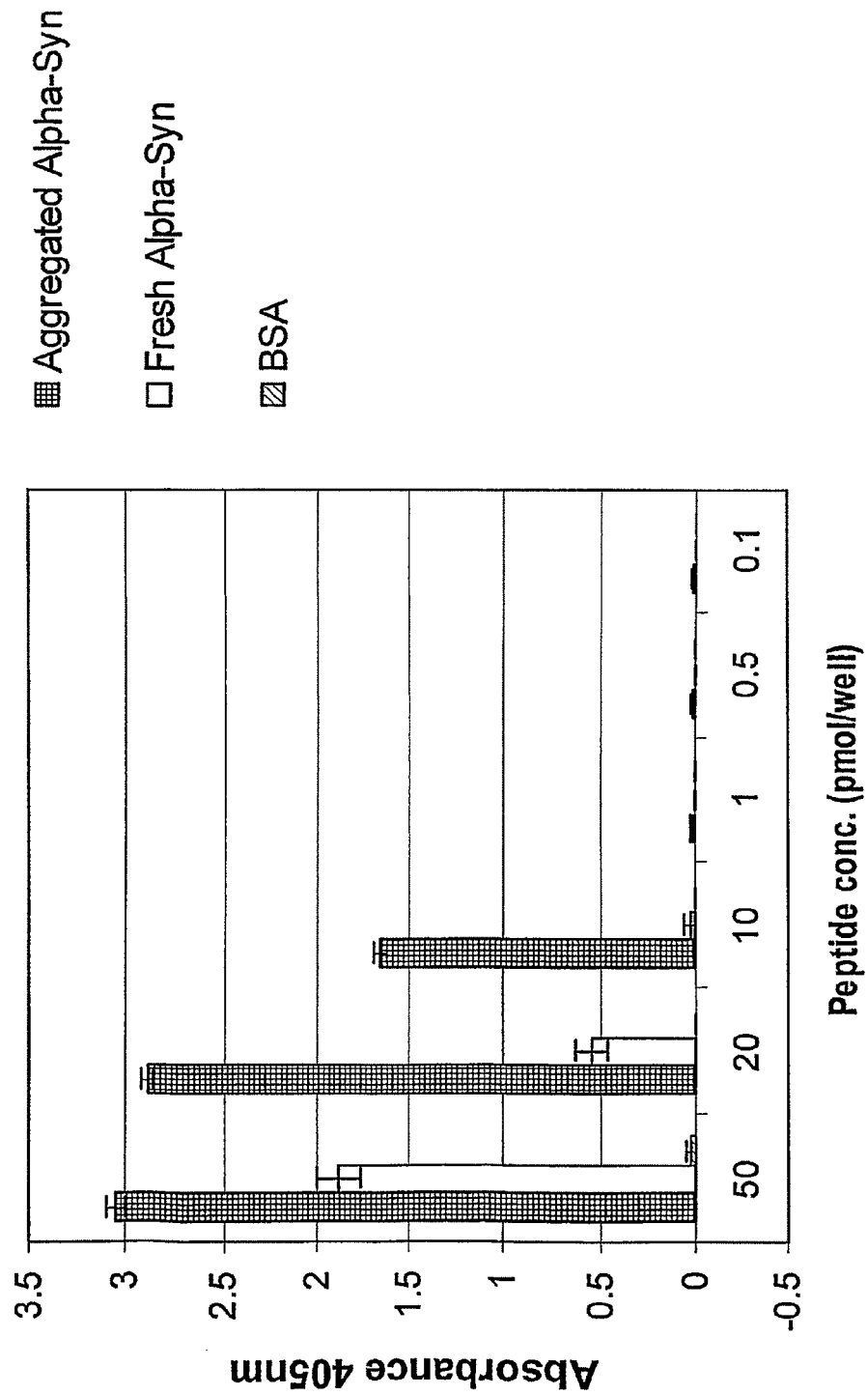

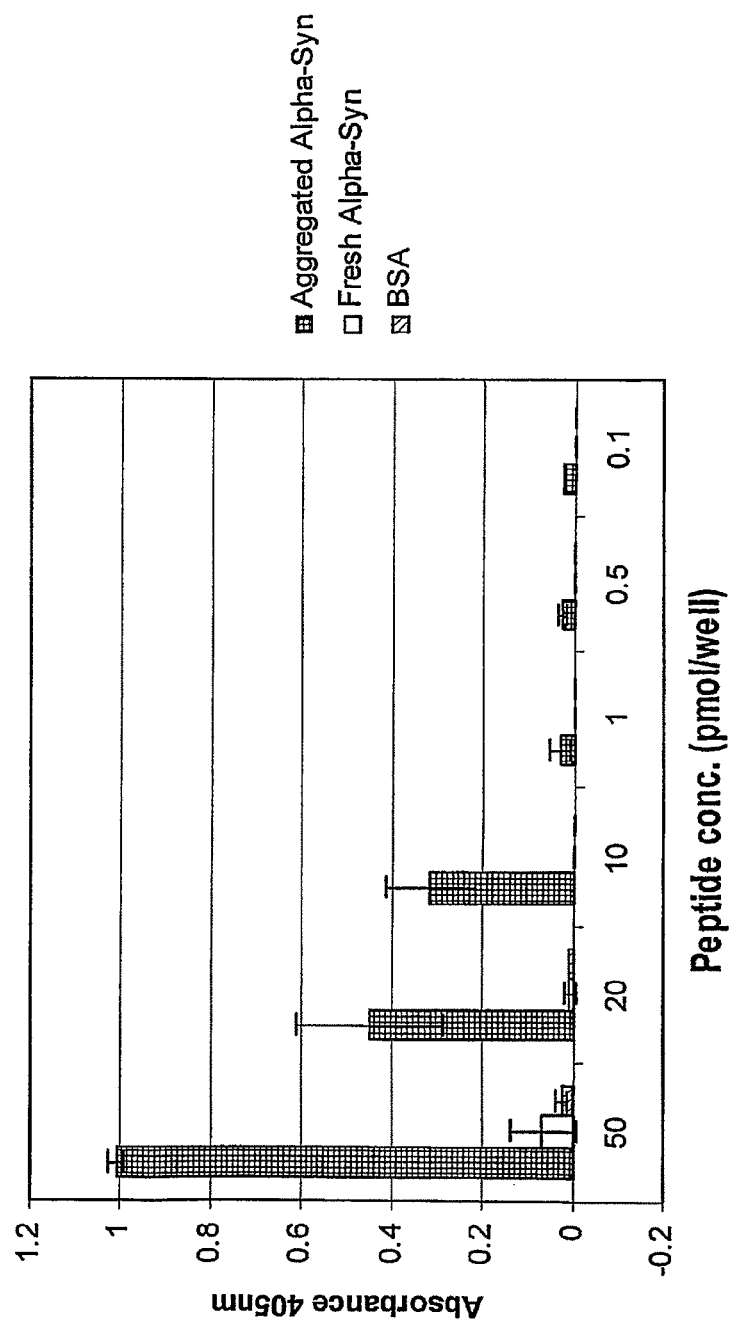

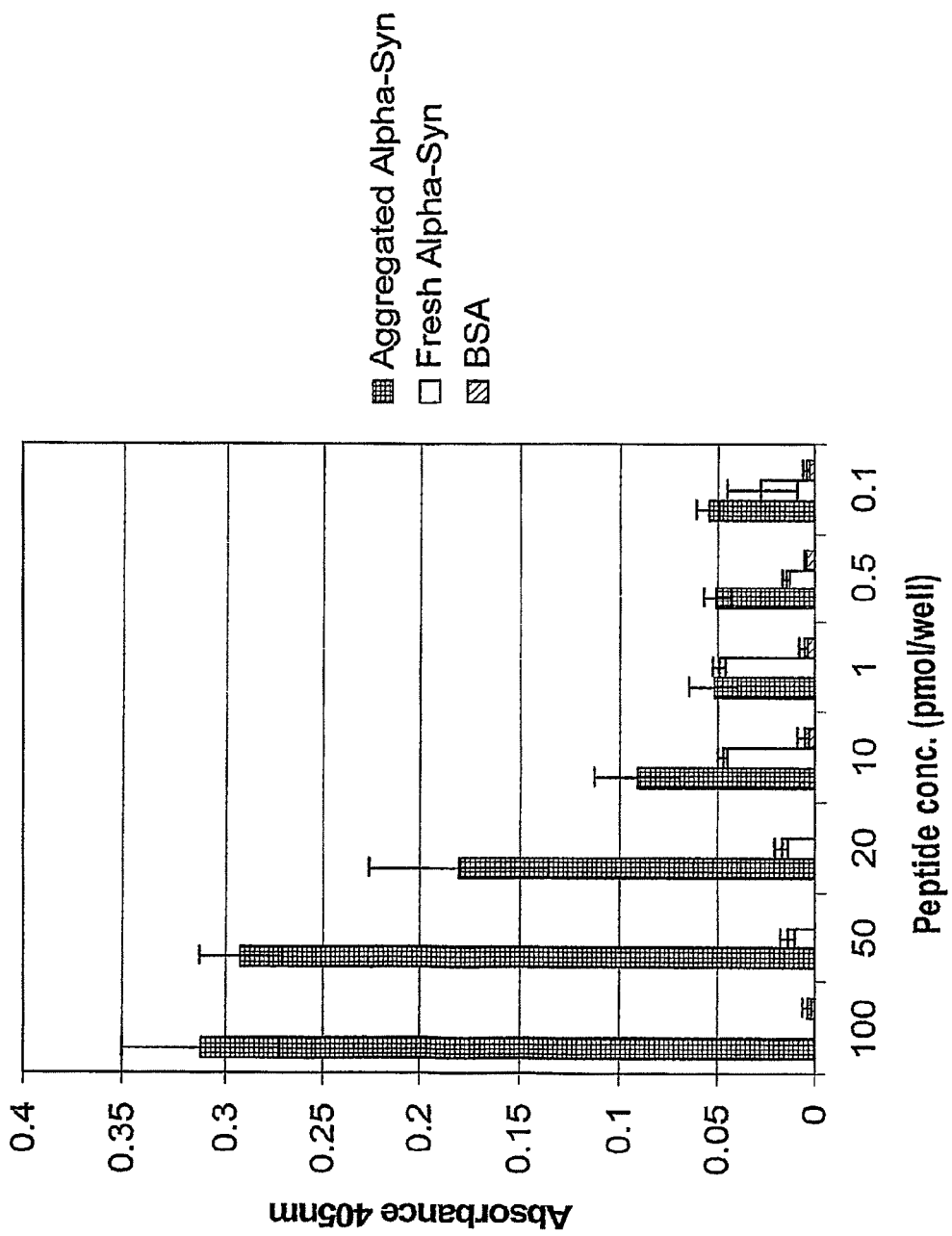

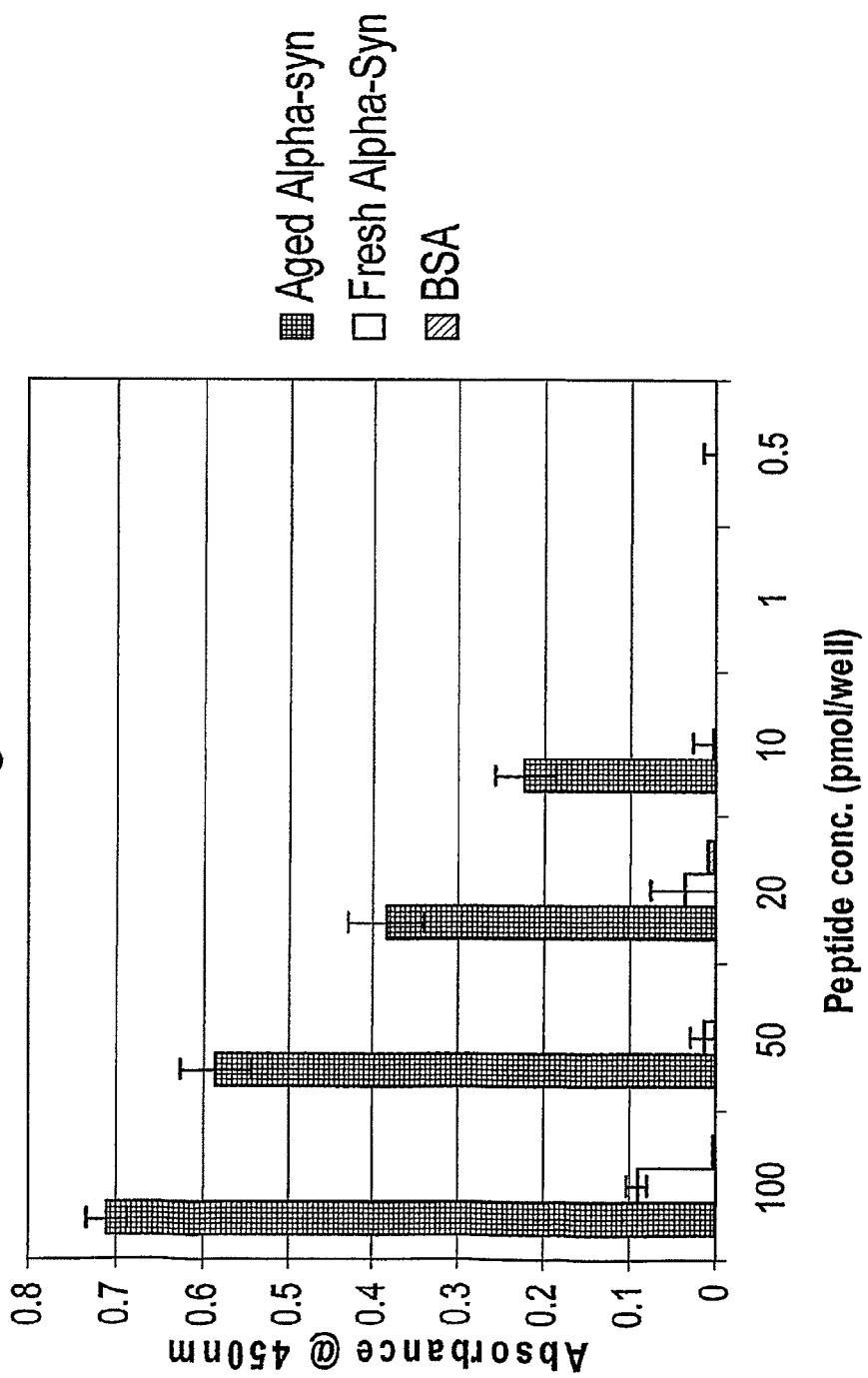

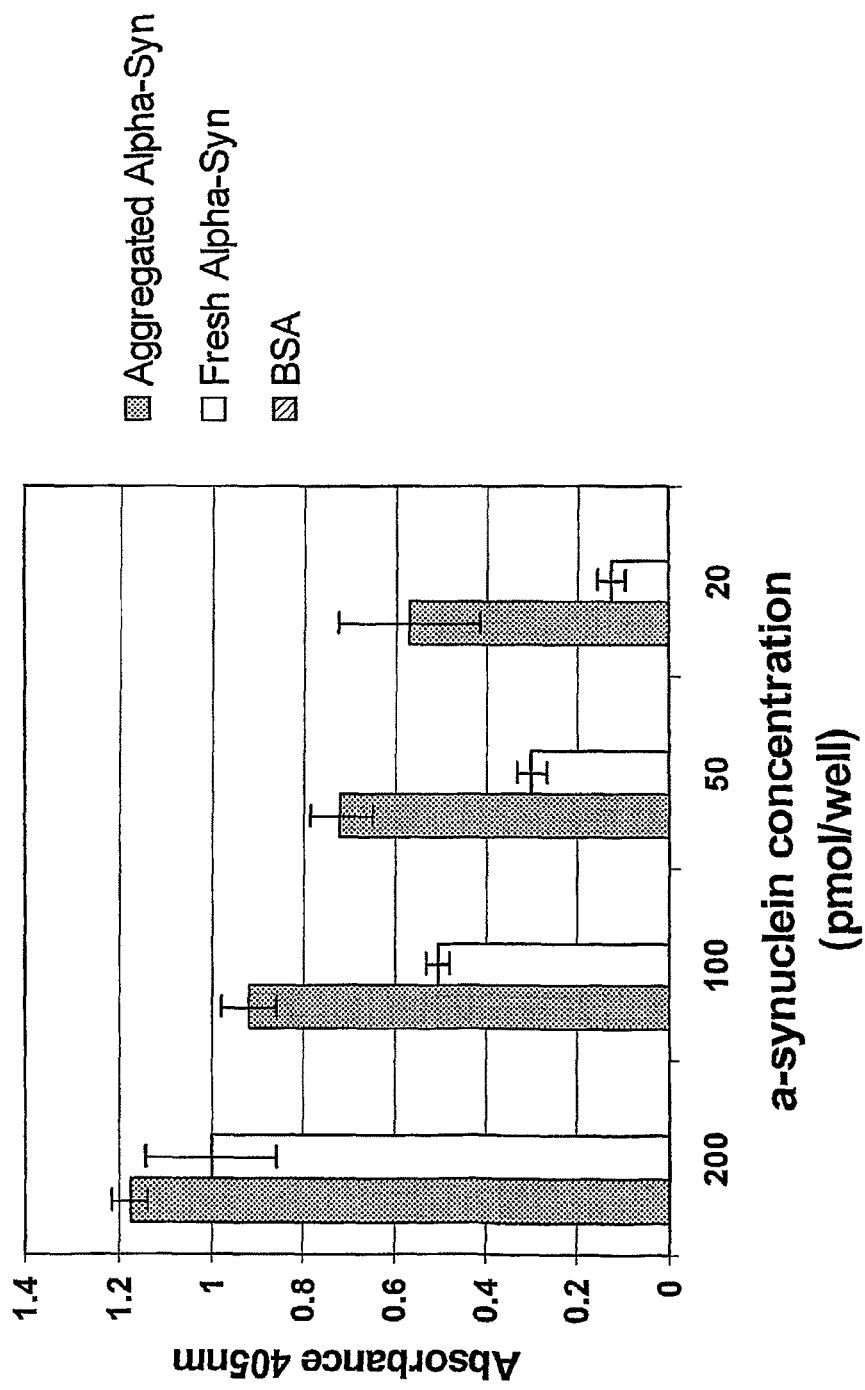

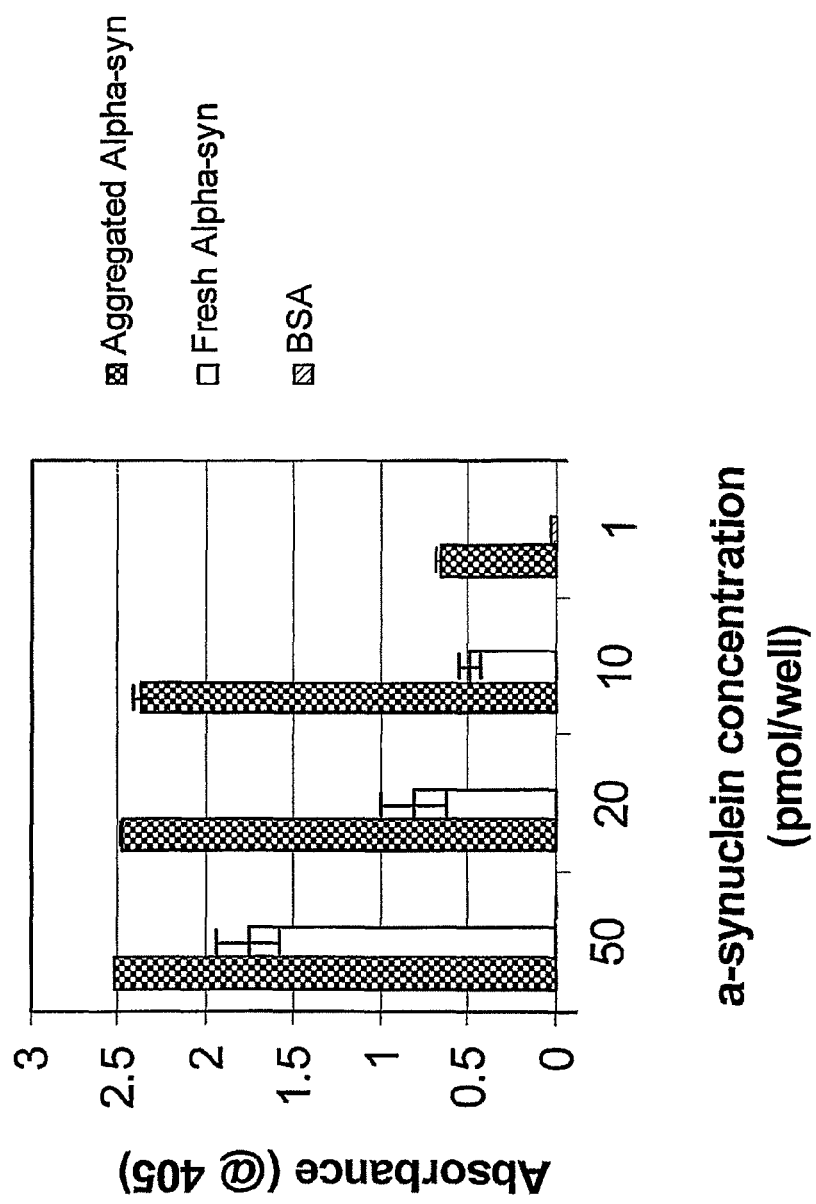

Fig. 13A.
Fig. 13B.
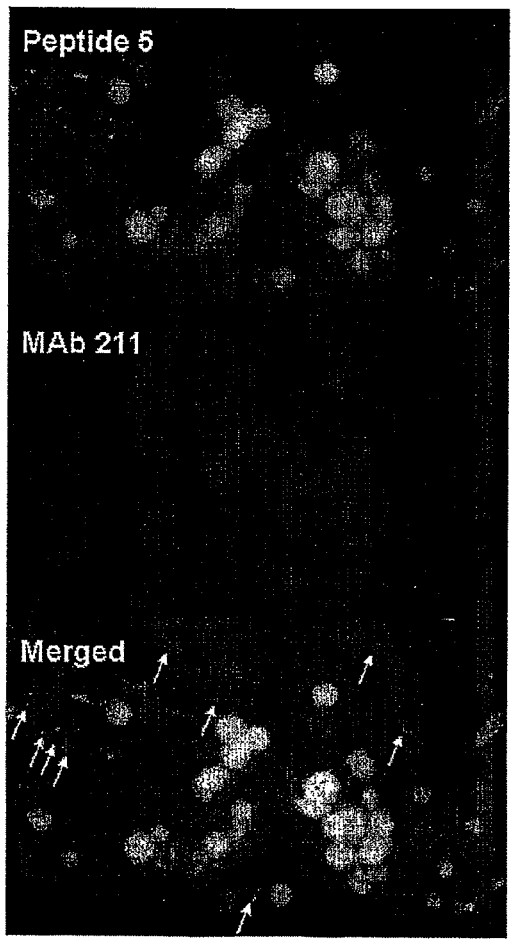
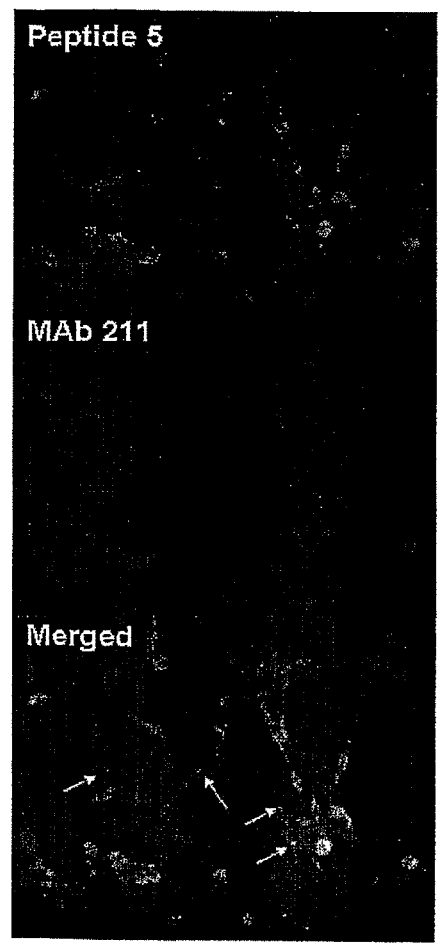

DIAGNOSTIC AGENT

FIELD OF THE INVENTION

The present invention relates to peptides capable of recognising and binding to α-synuclein aggregates and to the use of the peptides in the diagnosis and monitoring of synucleinopathic diseases (synucleinopathy diseases or synucleinopathies), which are neurodegenerative diseases involving abnormalities in one or more of the synucleins.

BACKGROUND OF THE INVENTION

The present invention relates to peptides and their derivatives which are useful for the diagnosis and monitoring of synucleinopathies. These are diseases associated with abnormalities in one or more of the synucleins and include some important neurodegenerative conditions, for example Parkinson's disease (PD), dementia with Lewy bodies (DLB), Alzheimer's disease (AD) and multiple system atrophy (MSA). The synucleins are also expressed at abnormally high levels in various tumours (e.g. breast, ovarian) in human cancer.

The synucleins are a family of small proteins (~14 kDa) that are expressed at high levels in nervous tissue. The three members of the family (α-, β-, and γ-synuclein) are the products of three genes present on different chromosomes. Convergent genetic and biochemical evidence suggests that the deposition of insoluble α-synuclein aggregates or fibrils is an important step in the development of several synucleinopathies.

The first indication of an involvement of α-synuclein in the pathogenesis of disease came from the isolation of one of its proteolytic fragments from purified amyloid of Alzheimer's diseased (AD) brains. This α-synuclein fragment, representing about 10% of the sodium dodecyl sulphate (SDS) insoluble material, was named non-Aβ-component of AD amyloid (NAC). Amino acid sequencing revealed that NAC comprised at least 35 amino acids, although the N-terminal residues could not be assigned with certainty because of the specificity of the enzyme used in sequencing. These 35 amino acids were later shown to correspond to residues 61-95 of a 140 amino-acid precursor (NACP). NACP was found to be identical with the protein called α-synuclein.

A clear genetic link with PD was established when it was shown that three different mutations in the α-synuclein gene were found in rare inherited forms of this disease. One mutation, α-synuclein (A53T), has been found in certain Italian and Greek families, and results in an Ala53 to Thr substitution. The other mutation, α-synuclein (A30P), has been found in a family of German origin, and results in an Ala30 to Pro change, and the last mutation E46K was found in familial Parkinsonism and DLB. Furthermore, Genetic duplications and triplications of the SNCA locus have also been reported in familial cases of PD suggesting that increase in gene dosage of SNCA, which concurrently results in an increase in levels of wild-type α-synuclein protein, is also pathogenic. Duplications of SNCA closely resemble idiopathic PD with late-age onset, slow progression and the absence of dementia and cognitive decline. Alternatively, SNCA triplications, result in early-onset PD with faster progression and dementia.

Additionally, lesions in the brain known as 'Lewy bodies' and 'Lewy neurites' constitute the main pathological features in the brains of patients with PD and DLB. These Lewy bodies and Lewy neurites contain α-synuclein aggregates. Additional immunohistochemical and immunoelectron microscopy studies have shown that α-synuclein is also associated with pathological lesions in other neurodegenerative diseases, sometimes involving non-neuronal cells, such as the glial cytoplasmic inclusions found in MSA. Thus PD, AD, DLB and MSA are herein referred to collectively as synucleinopathies.

It has recently been reported that lesions similar to those found in the human synucleinopathic diseases can be created in transgenic animals. The transgenic animals express high levels of human wild-type or mutant α-synuclein protein and progressively develop many of the pathological conditions associated with synucleinopathic diseases. These findings implicate α-synuclein protein aggregate deposition in the pathophysiology of the synucleinopathic diseases. Interestingly, the three human α-synuclein mutations appear to accelerate the aggregation process. The full amino acid sequence of human wild-type α-synuclein is provided as SEQ. ID No. 1.

SUMMARY OF THE INVENTION

Small peptide inhibitors of α-synuclein aggregation and toxicity have been designed, and were named α-synuclein inhibitors (ASI). These short peptides contain part of the binding region of α-synuclein corresponding to residues 69-72 of SEQ ID NO: 1. The insolubility of these peptides was overcome by placing hydrophilic residues, such as arginine and glycine, at the N-terminal and glycine and arginine at the C-terminal of the synthetic peptides. These peptides were found to bind to the monomeric (free) forms of α-synuclein and were able to block its assembly into both early soluble aggregates (or adducts) and mature aggregates (or mature synuclein fibrils).

According to the present invention there is provided a peptide comprising or consisting essentially of an amino acid sequence corresponding to the amino acid sequence of the binding region of human wild-type α-synuclein (i.e. residues 61 to 95 of SEQ ID NO:1). The sequence of the binding region is provided in full below, and as SEQ ID NO:2.
Sequence of the Binding Region of α-Synuclein:

```
                                          (SEQ ID No. 2)
EQVTNVGGAV VTGVTAVAQK TVEGAGSIAA ATGFV
```

Preferably the peptide comprises or consists of the amino acid sequence of from 2 to 12 contiguous amino acid residues from the sequence corresponding to amino acid residues 61 to 95 of SEQ ID NO:1. Specifically, the peptide may comprise or consist of an amino acid sequence of 2, 3, 4, 5, 6, 7, 8, 9 10, 11 or 12 contiguous amino acid residues from the sequence corresponding to amino acid residues 61 to 95 of SEQ ID NO:1. Most preferably, the peptide may comprise or consist of an amino acid sequence comprising a maximum of seven contiguous amino acid residues, a maximum of six contiguous amino acid residues, a maximum of five contiguous amino acid residues, a maximum of four contiguous amino acid residues, a maximum of three contiguous amino acids, or a maximum of two contiguous amino acid residues from the sequence corresponding to amino acid residues 61 to 95 of SEQ ID NO: 1.

The present invention is based upon the surprising finding that ASIs peptides derived from the sequence of the binding region of naturally occurring α-synuclein (amino acid residues 61 to 95 of SEQ ID NO: 1) bind with higher affinity to both early soluble aggregates and mature aggregates of α-synuclein than to free α-synuclein "monomeric form of α-synuclein". Accordingly, a peptide comprising or consisting essentially of amino acid sequences corresponding to the binding region of α-synuclein can be used to detect aggregates of α-synuclein (or its fragments such as NAC). Unless otherwise stated, all subsequent references to α-synuclein aggregates should be taken also to apply to both early soluble (low and/or high molecular weight of soluble oligomers) and mature aggregates of α-synuclein or its fragments or derivatives, including aggregates comprising α-synuclein complexed with any other protein(s).

As a result of the ability to bind to α-synuclein aggregates, a peptide according to the invention is suitable for use in the diagnosis of diseases involving α-synuclein. Since the peptide of the invention is able to bind the soluble aggregates (or adducts) of α-synuclein which are present at the early stages of synucleinopathic diseases, the peptide is particularly suitable for use in the early diagnosis of such diseases. The peptide is useful for detecting aggregates of "wild-type" α-synuclein (native form), or mutated, nitrated, phosphorylated, glycosylated or truncated forms or any other naturally occurring modified forms.

The peptide of the invention may additionally comprise a substituent to increase transport across the blood-brain barrier and/or increase uptake by living cells. In addition, the peptide of the invention may be labelled for use as imaging agents. For example, an additional, preferably amino-terminal, substituent such as 1,4,7,10-tetraazacyclododecane-1,4,7-tris(acetic acid-t-butyl ester)-10-acetic acid (DOTA) may be introduced to provide a ligand for complexing with a contrast agent such as gadolinium ions, to enable MRI imaging of α-synuclein aggregate deposits in patients.

The peptide of the invention thus has excellent properties as agents for use in the diagnosis of early or moderate synucleinopathic diseases and for monitoring therapy of synucleinopathic diseases. Accordingly, the present invention provides:

An agent for use in a diagnostic method practiced on the human or animal body wherein the agent comprises a peptide comprising the amino acid sequence of from two to twelve contiguous amino acid residues from the sequence corresponding to amino acid residues 61 to 95 of SEQ ID NO:1, or comprises a derivative or analogue of said amino acid sequence, wherein the agent binds to α-synuclein aggregates with a higher affinity than to free α-synuclein.

A peptide comprising:
  i) the amino acid sequence DThr-DVal-DVal-DAla or DVal-DVal-DAla;
  ii) a poly-D-Arginine peptide linked to the N- or C-terminus of the sequence of (i) by a Glycine or N-methlyglycine residue and/or any other spacer; and
  iii) the substituent DOTA linked to the N-terminus of the peptide.

An agent or peptide of the invention for use in the diagnosis of a synucleinopathic disease involving α-synuclein and/or fragment(s) of α-synuclein.

A method of diagnosing a synucleinopatic disease involving α-synuclein and/or fragment(s) of α-synuclein, said method comprising administering an agent of the invention to a subject and thereby detecting the presence or absence of α-synuclein aggregates, wherein the presence of α-synuclein aggregates indicates that the subject has a synucleinopathic disease and the absence of α-synuclein aggregates indicates that the subject does not have said synucleinopathic disease.

A method of monitoring a synucleinopathic disease involving α-synuclein and/or fragment(s) of α-synuclein, said method comprising administering an agent of the invention to a subject and detecting the amount and/or size of any α-synuclein aggregates.

A kit for imaging α-synuclein aggregates, said kit comprising an agent of the invention and means for administering the agent to a subject.

An in vitro method of diagnosing a synucleinopathic disease involving α-synuclein and/or fragment(s) of α-synuclein in a patient comprising:
  (a) combining a sample of tissue and/or biological fluid (e.g. blood, CSF, urine) from the patient with an agent of the invention for a time and under conditions effective to allow binding of the agent to aggregates of α-synuclein present in the sample; and
  (b) thereby detecting the presence or absence of aggregates of α-synuclein in the sample, wherein the presence of α-synuclein aggregates indicates that the subject has a synucleinopathic disease and the absence of α-synuclein aggregates indicates that the subject does not have said synucleinopathic disease.

An in vitro method of monitoring the effectiveness of a therapeutic agent that has been administered for the purpose of treating a synucleinopathic disease involving α-synuclein and/or fragment(s) of α-synuclein, the method comprising analysing a sample from an animal model for the presence and amount of aggregates of α-synuclein.

A method of monitoring the effectiveness of a therapeutic agent that has been administered for the purpose of treating a synucleinopathic disease involving α-synuclein and/or fragment(s) of α-synuclein, the method comprising imaging the brain of an animal model for the presence and amount of α-synuclein aggregates.

BRIEF DESCRIPTION OF THE FIGURES

FIG. 1 illustrates structure of an exemplary imaging reagent of the invention (Imaging Agent 1). The imaging reagent contains three domains: the α-synuclein-binding domain is the retroinverso sequence in the middle section of the reagent; the transport domain is the polyamine or poly D-arginine at the C-terminus; and the contrast agent is the gadolinium ion at the N-terminus.

FIGS. 4 A and B show that the peptide binds more effectively to preformed α-synuclein aggregates than unaggregated, fresh α-synuclein at a range of α-synuclein concentrations when the peptides are coated on microtiter plates and α-synuclein solution is added to the wells.

FIG. 13 shows that the peptides bind to α-synuclein aggregates in a cell model.

DESCRIPTION OF THE SEQUENCES MENTIONED HEREIN

Figure 2A:
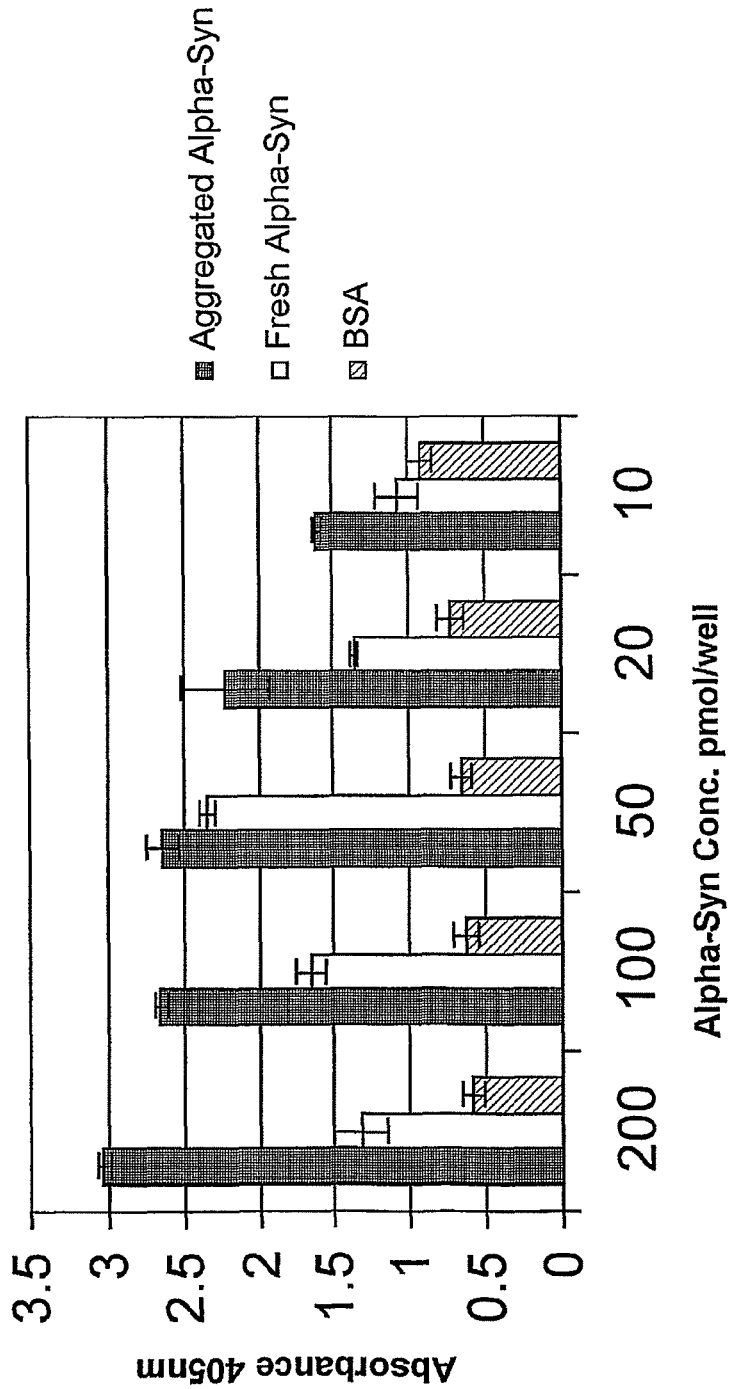
FIG. 2 shows that peptides OR1 to 4 (respectively) of the invention bind more effectively to preformed α-synuclein aggregates than unaggregated, fresh α-synuclein at a range of α-synuclein concentrations when the α-synuclein is coated on microtiter plates and peptide solution is added to the wells.

SEQ ID NO: 1 corresponds to the full sequence of human wild-type α-synuclein. SEQ ID NO: 2 corresponds to the binding region of α-synuclein. SEQ ID NOS: 3 to 7 correspond to preferred peptide sequences of the invention.

DETAILED DESCRIPTION OF THE INVENTION

α-Synuclein Aggregates

Unless otherwise stated, the term α-synuclein aggregates is intended to cover both early soluble aggregates (adducts or soluble oligomers of low and/or high molecular weight) and mature insoluble aggregates (or mature amyloid fibrils) of α-synuclein, and any fragments or derivatives thereof. Aggregates are considered to comprise any abnormal conformation or accumulation of α-synuclein monomers, and may also comprise other components such as ubiquitin, neurofilament protein, and alpha B crystalline.

Unless otherwise stated, the term free α-synuclein is intended to refer to soluble α-synuclein monomers in a natural conformation.

Agent

The present invention provides an agent that binds to α-synuclein, and in particular to α-synuclein aggregates. The agent comprises an α-synuclein aggregate-binding domain which comprises a peptide sequence from the binding region of α-synuclein (residues 61 to 95 of SEQ ID NO:1), and a detectable label. The agent may optionally comprise a transport domain to facilitate transport of the peptide across the blood brain barrier and/or uptake of the peptide by living cells. Agents of the invention are useful in detecting α-synuclein aggregates and are useful in the diagnosis of synucleinopathic diseases, including PD, DLB and MSA.

α-Synuclein Aggregate-Binding Domain

The peptides comprise from three to thirty-five amino acid residues. Preferably the peptide sequence comprises a maximum of seven amino acid residues, more preferably a maximum of six amino acid residues, even more preferably a maximum of five amino acid residues, and most preferably a maximum of three amino acid residues.

Preferably the peptide comprises or consists of the amino acid sequence of from 2 to 12 contiguous amino acid residues from the sequence corresponding to amino acid residues 61 to 95 of SEQ ID NO:1. Specifically, the peptide may comprise or consist of an amino acid sequence of 2, 3, 4, 5, 6, 7, 8, 9 10, 11 or 12 contiguous amino acid residues from the sequence corresponding to amino acid residues 61 to 95 of SEQ ID NO:1. Most preferably, the peptide may comprise or consist of an amino acid sequence comprising a maximum of seven contiguous amino acid residues, a maximum of six contiguous amino acid residues, a maximum of five contiguous amino acid residues, a maximum of four contiguous amino acid residues, a maximum of three contiguous amino acids, or a maximum of two contiguous amino acid residues from the sequence corresponding to amino acid residues 61 to 95 of SEQ ID NO: 1.

In a preferred embodiment, the peptide comprises or consists of an amino acid sequence of from 2 to 7 contiguous amino acid residues from the sequence corresponding to amino acid residues 67 to 73 of SEQ ID NO: 1, i.e. Gly-Gly-Ala-Val-Val-Thr-Gly (SEQ ID NO: 3). Specifically, the peptide may comprise or consist of 2, 3, 4, 5, 6 or 7 contiguous amino acid residues from the sequence corresponding to amino acid residues 67 to 73 of SEQ ID NO: 1. Most preferably the peptide comprises or consists of 3 contiguous amino acid residues from the sequence corresponding to amino acid residues 67 to 73 of SEQ ID NO:1, i.e 3 contiguous amino acid residues from SEQ ID NO: 3. In particular the peptide may comprise or consist essentially of the amino acid sequence of all seven contiguous amino acids of SEQ ID NO: 3, or the amino acid sequence of the tetrapeptide Gly-Ala-Val-Val (SEQ ID NO: 4), the pentapeptide Ala-Val-Val-Thr-Gly (SEQ ID NO: 5), the tetrapeptide Val-Val-Thr-Gly (SEQ ID NO: 6), or the tripeptide Val-Thr-Gly (SEQ ID NO: 7). The peptide may comprise or consist essentially of the amino acid sequence of two contiguous amino acids from the sequence corresponding to amino acid residues 61 to 95 of SEQ ID NO: 1. For example, the peptide may comprise or consist essentially of the amino acids sequence VT or TG (corresponding to residues 71 to 72 or 72 to 73 respectively of SEQ ID NO:1).

Examples of peptide sequences in accordance with the invention are shown in the left hand column of Table 1 below, which also identifies the residues of α-synuclein from which the peptide sequence is derived.

TABLE 1

| Sequence | Position of contiguous sequence in α-synuclein. |
| --- | --- |
| SEQ ID NO: 3<br>GGAVVTG | 67-73 |
| SEQ ID NO: 4<br>GAVV | 68-71 |
| SEQ ID NO: 5<br>AVVTG | 69-73 |
| SEQ ID NO: 6.<br>VVTG | 70-73 |
| SEQ ID NO: 7<br>VTG | 71-73 |

The sequence of contiguous amino acid residues from the sequence corresponding to amino acid residues 61 to 95 of SEQ ID NO:1 may be linked at the N-terminal and/or C-terminal end of the sequence to one or more further amino acid residues which are more hydrophilic than the amino acid residue to which that end of the sequence is linked in the native sequence of human wild-type α-synuclein. Glycine (Gly) residues may optionally be used as linkers/spacer between the binding sequence and the additional amino acid residues.

Derivatives or analogues of the peptides of the invention are also effective for binding to the aggregates of synucleins. Therefore, according to a second aspect of the invention there is provided a derivative or analogue of a peptide according to the first aspect of the invention.

Derivatives or analogues of peptides according to the invention may include N-substituted derivatives. The substituent may, for example, be a hydroxyl or ethyl group but is more preferably a methyl group. Thus examples of derivatives or analogues of peptides according to the invention include N-methylated derivatives of the peptides. Such N-methylated derivatives include derivatives in which some or all of the sequence are N-methylated amino acid residues. It is preferred that substitution is at the α-position.

Derivatives or analogues of peptides according to the first aspect of the invention may further include D-amino acid derivatives of the peptides, peptoid analogues of the peptides, or peptide-peptoid hybrids.

Peptides may be subject to degradation by a number of means (such as protease activity in biological systems). Such degradation may limit their bioavailability, and hence their ability to bind to synuclein aggregates. There are wide ranges of well established techniques by which peptide derivatives that have enhanced stability in biological contexts can be designed and produced. Such peptide derivatives may have improved bioavailability as a result of increased resistance to protease-mediated degradation.

Preferably a peptide derivative or analogue according to the second aspect of the invention is more protease-resistant than the peptide from which it is derived. Protease-resistance of a peptide derivative and the peptide from which it is derived may be evaluated by means of well-known protein degradation assays. The relative values of protease resistance for the peptide derivative and peptide may then be compared.

In peptoid residues, the position of the side chain is shifted from the α-carbon atom to the nitrogen atom. The identity of the side chain is conserved, while the orientation in three-dimensional space is reversed. These compounds may be considered a combination of backbone and side chain modifications. Peptoid compounds have two properties that make them suitable for use as peptide derivatives/analogues according to the invention:

(i) In peptoid residues no hydrogen bond involving the NH would be possible.

(ii) The peptoids are resistant to enzymatic degradation.

Peptoid derivatives of the peptides of the invention may be readily designed from knowledge of the structure of the chosen peptide. Commercially available software may be used to develop peptoid derivatives according to well-established protocols.

It has been reported that a retropeptoid, (in which all amino acids were replaced by peptoid residues in reversed order) is able to mimic a high-affinity binder. A retropeptoid is expected to bind in the opposite direction in the ligand-binding groove, as compared to a peptide or peptoid-peptide hybrid containing one peptoid residue. As a result, the side chains of the peptoid residues are in the same orientation as the side chains in the original peptide.

Peptide-peptoid hybrid peptidomimetics can also be used to detect α-synuclein aggregates. Such hybrids comprise peptides in which one or more amino acids have been replaced by the corresponding peptoid residues.

In another embodiment of the second aspect of the invention the sequence comprises D-amino acids. The order of the sequence of D-amino acids can also be reversed as compared to the section of the sequence of α-synuclein on which it is based. For example a D-amino acid based peptide derivative with a sequence based on residues 69 to 71 of α-synuclein (GAVV) could have a sequence of GAVV or VVAG.

Peptides, peptide derivatives and peptide analogues according to the invention may be adapted to facilitate their entry into cells, or across biological barriers (such as the blood brain barrier). Since synucleinopathies commonly involve pathological activity of synucleins in the brain, facilitating the entry of peptides or peptide derivatives of the invention into this tissue is highly desirable.

Transport Domain

The transport domain may also comprise or consist of any compound or substituent which facilitates transport of the peptide across the blood brain barrier and/or uptake of the peptide by living cells. Methods have been developed for the delivery of exogenous proteins into living cells and across the blood-brain barrier with the help of membrane-permeable carrier peptides such as HIV-1 Tat-(48-60), flock house virus (FHV) coat-(35-49), *Drosophila* Antennapedia-(43-58) and Basic peptides such as octa and hexa arginine peptides. By genetically or chemically hybridising these carrier peptides, the efficient intracellular delivery of various oligopeptides and proteins has been achieved. The efficacy of such approaches is illustrated by the example of the Tat-β-galactosidase fusion protein, which has a molecular mass as high as 120 kDa. Expression of this fusion protein in mice results in delivery of the biologically active fusion protein to all tissues, including the brain. Thus peptides or peptide derivatives of the invention may be adapted in order to increase their bioavailability in cells or tissues by the incorporation of such carrier peptides.

This approach, using carrier peptides to improve availability of peptides, peptide derivatives and peptide analogues of the invention is particularly suitable for allowing the incorporation into tissues or cells of molecules containing unnatural amino acids (e.g. D-amino acids or N-methylated amino acids) or non-peptide derivatives.

Furthermore, preferred transport domains comprise guanidine groups. In one preferred embodiment, the transport domain comprises a diamine. The polyamine typically comprises 2, 3, 4, 5, 6, 7, 8 or 9 amines. The polyamines may be synthetic or naturally occurring. The polyamine is typically one capable of interacting with the polyamine transporter at the blood brain barrier. Useful polyamines include 1,4 butadiamine, 1, 5 pentadiamine, putrescine, spermidine, 1,3-diaminopropane, norspermidine, spermine, syn-homospermidine, thermine, thermospermine, caldopentamine, homocaldopentamine and canavalmine.

In an alternative embodiment, the transport domain may comprise a diguanidine. The polyguanidine may comprise from 3 to 10 guanidines, for example, 4, 5, 6 or 7 guanidines.

In an alternative embodiment the transport domain may be a polyarginine comprising, for example, 6 arginine residues (polyarginine[$r_6$])

The suitability of a transport signal for inclusion in an agent of the invention may readily be determined by a person skilled in the art. For example, the blood brain barrier permeability of an agent comprising a potential transport signal may be determined in an experimental animal, such as a mouse, by quantifying the permeability co-efficient X surface area (PS) product for each protein. Typically PS is measured after correction for the residual plasma volume ($V_p$) occupied by the protein in blood vessels in different brain regions following an intravenous bolus injection.

The transport signal may be present at either the N-terminal end or at the C-terminal end of the α-synuclein aggregate-binding peptide.

The amine or guanidine transport signal may be attached to the peptide by any suitable method, for example, by chemical cross-linking. Suitable cross-linkers are well known in the art. One such method is described in Example 1.

Detectable Label

The α-synuclein aggregate-binding peptide of the invention is labelled to facilitate imaging of α-synuclein aggregates. The peptide may, for example, include a detectable label at the C-terminus and/or at the N-terminus. In one preferred embodiment, the detectable label is present at the N-terminus. The detectable label is typically one which enables the detection of the peptide when bound to α-synuclein aggregates. The α-synuclein aggregates may be present in the brain of a living mammal or in a post-mortem brain sample. Useful labels include radiolabels and contrast agents, preferably ones suitable for use in humans.

Suitable radiolabels include $^{18}F$, $^{123}I$, $^{111}In$, $^{131}I$, $^{99m}Tc$, $^{32}P$, $^{125}I$, $^{32}P$, $^{125}I$, $^{3}H$, $^{14}C$ and $^{188}RL$. Suitable contrast agents include rare earth ions such as gadolinium (Gd), dysprosium and iron. Other examples of such contrast agents include a number of magnetic agents paramagnetic agents and ferromagnetic or superaramagnetic agents, such as particles.

Other labels that may be used include fluorescent labels such as fluorescein and rhodamine, nuclear magnetic resonance active labels, positron emitting isotopes detectable by a positron emission tomography ("PET") scanner, chemiluminescers such as luciferin and enzymatic markers such as peroxidase or phosphatase. Short-range radiation emitters, such as isotopes detectable by short-range detector probes can also be employed.

Peptides of the invention may be labelled using standard techniques. For example, the peptides may be iodinated using 1,3,4,6-tetrachloro-3α,6α-diphenylglycouril or chloramine T.

Chelates (e.g., EDTA, DTPA and NTS chelates) can be used to attach (and reduce toxicity) of some paramagnetic substances (e.g., $Fe^{+3}$, $Mn^{+2}$, $Gd^{+3}$). Peptides can be labelled with gadolinium ions, for example, by conjugating a low molecular Gd chelate such as 1,4,7,10-tetraazacyclododecane-1,4,7-tris(acetic acid-t-butyl ester)-10-acetic acid (DOTA) or diethylene triamine pentaacetic acid (DTPA) to the peptide. Accordingly, in one embodiment an agent of the invention may comprise the peptide Gly-X-DVal-DVal-DAla-Gly, wherein X is either absent or DThr, a transport signal and a low molecular weight chelate, such as DOTA. In one embodiment of the invention, the detectable label may be one which is suitable for detection by microscopy, such as electron microscopy, confocal microscopy or light microscopy. The detectable label may, for example, be biotin, a fluorescent compound, such as green fluorescent protein, or a peptide tag, such as a his tag, myc or flag.

Imaging Methods

Agents of the invention comprising a detectable label are useful in methods of imaging α-synuclein aggregates. Accordingly, the present invention provides a method of imaging α-synuclein aggregates, which method comprises detecting the binding of an agent of the invention to α-synuclein aggregates.

The presence or absence of the α-synuclein aggregates may be detected in the brain in vivo using any suitable imaging techniques. In such embodiments, the method may further comprise administering an agent of the invention to a subject. The subject is typically a mammal, preferably a human. The subject may be an experimental animal and, in particular, an experimental animal model of synucleinopathic disease. Animal models of, for example, PD are known in the art and include transgenic mice and transgenic *Drosophilia.*

Suitable imaging techniques include positron emission tomography (PET), gamma-scintigraphy, magnetic resonance imaging (MRI), functional magnetic resonance imaging (FMRI), magnetoencephalography (MEG) and single photon emission computerized tomography (SPECT). MRI is a preferred method because the spatial resolution and signal-to-noise ratio provided by MRI (30 μm) is suitable for detecting α-synuclein aggregate deposits.

Magnetic Resonance Imaging (MRI) uses NMR to visualise internal features of a living subject, and is useful for prognosis, diagnosis, treatment, and surgery. MRI can be used without radioactive tracer compounds for obvious benefit. Some MRI techniques are summarised in published European patent application EP-A-0 502 814. Generally, the differences related to relaxation time constants T1 and T2 of water protons in different environments is used to generate an image. However, these differences can be insufficient to provide sharp high resolution images. The differences in these relation time constants are enhanced by contrast agents.

The presence or absence of the α-synuclein aggregates may also be detected in vitro, for example, in experiments designed to identify agents that inhibit α-synuclein aggregate formation and deposition. Agents of the invention may also be used to detect α-synuclein aggregates in brain sections from experimental animals or in post-mortem brain sections from a human subject. In such embodiments, the imaging method may be microscopy, such as electron microscopy, confocal microscopy or light microscopy.

Agents of the invention may be used in methods of diagnosing synucleinopathies. In one preferred embodiment, agents of the invention are useful in diagnosing PD, DLB and MSA. Diagnosis of synucleinopathies in the mild or moderate stage is currently difficult because it relies on complex psychiatric profiling. Use of a labelled agent of the invention as an MRI-imaging agent will allow a decisive diagnosis to be made at early stages of the disease, when protective therapy can be instituted before widespread destruction of the brain has occurred. As a number of therapeutics are coming through trials for the purpose of ridding the brain of α-synuclein aggregate deposits, imaging (in particular MRI) using an imaging agent of the invention will provide a way of tracking the effectiveness of therapy.

In one embodiment, the invention provides a method for diagnosing synucleinopathic disease in a subject, the method comprising determining the presence or absence of α-synuclein aggregates, wherein the presence of α-synuclein aggregates indicates that the subject has synucleinopathic disease. The absence of A α-synuclein aggregates indicates that the subject does not have synucleinopathic disease.

The images obtained from a subject may be compared to images taken from control subjects who do not have synucleinopathic disease and/or to images from other subjects known to have synucleinopathies in order to reach or confirm a diagnosis.

A method of diagnosing synucleinopathic disease of the invention typically comprises administering a detectably labelled agent of the invention to a subject; imaging the brain of said subject to detect any of said agent bound to α-synuclein aggregates; and determining the presence or absence of α-synuclein aggregates. An agent of the invention is administered to a subject in need of diagnosis in an amount sufficient to bind to any α-synuclein aggregates and be detected by imaging techniques, such as MRI.

The invention also provides methods for monitoring the status of synucleinopathic disease in a subject. The methods may, thus, be used to determine disease progression. For example, the methods may be used to monitor growth of α-synuclein aggregate deposits in the brain of a subject. The method may also be used to monitor the effectiveness of therapy and/or to evaluate the efficacy of new synucleinopathic disease treatments. A subject may be tested on a regular basis, for example monthly, six monthly or yearly, to monitor disease progression within the subject.

Thus, in a further embodiment, the present invention provides a method for monitoring synucleinopathic disease in a subject, the method comprising determining the presence or absence of α-synuclein aggregates in the brain of the subject by detecting binding of an agent of the invention to the α-synuclein aggregates. The images are typically compared to one or more image taken from the same subject at an earlier time point.

The number and/or size of α-synuclein aggregates present in the brain of a subject correlates with synucleinopathic disease progression. An increase in the number and/or size of α-synuclein aggregates indicates a progression of the disease. Conversely, a decrease in the number or size of α-synuclein aggregates indicates disease regression. Where no change is observed in the number and/or size of α-synuclein aggregates, the disease is in a steady state. Where the monitoring method is determine the efficacy of a treatment for synucleinopathic disease, maintenance of a steady state or a decrease in the number or size of α-synuclein aggregates typically indicates that the treatment is successful. Levels of α-synuclein aggregates may be compared to standards to determine synucleinopathic disease status.

Formulation and Administration of the Agent for Use in Methods of Diagnosis

The formulation of any of the agent will depend upon factors such as the nature of the agent and the condition to be diagnosed. Any such agent may be administered or delivered in a variety of dosage forms. It may be administered or delivered by non-surgical or surgical means. Non-surgical means of administration include, for example, administration orally (e.g. as tablets, troches, lozenges, aqueous or oily suspensions, dispersible powders or granules), topically, transdermally or by infusion or inhalation techniques. Surgical means of administration include, for example, administration parenterally, subcutaneously, intravenously, intramuscularly, or intrasternally. The agent may also be administered or delivered as suppositories. A physician will be able to determine the required route of administration or delivery for each particular patient.

The agent may be administered directly to the site of an α-synuclein aggregate deposit, e.g. a Lewy body, typically by injection into a blood vessel supplying the brain or into the brain itself.

Typically the agent is formulated with a pharmaceutically acceptable carrier or diluent. The invention provides a pharmaceutical composition comprising an agent of the invention and a pharmaceutically effective diluent or carrier.

The pharmaceutical carrier or diluent may be, for example, an isotonic solution. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous or infusions may contain as carrier, for example, sterile water or preferably they may be in the form of sterile, aqueous, isotonic saline solutions.

The dose may be determined according to various parameters, especially according to the substance used; the age, weight and condition of the patient to be treated; the route of administration; and the diagnostic method to be used. Again, a physician will be able to determine the required route of administration and dosage for any particular patient.

Kits

The invention also provides kits for carrying out the diagnostic and monitoring methods of the invention. The kit may comprise an imaging agent of the invention and means for administering the imaging agent to a subject. Means for administering the agent may comprise or consist of a sterile syringe. Instructions for using the kit to monitor or diagnose synucleinopathic disease may also be included.

The following Examples illustrate the invention.

EXAMPLE 1

Synthesis and Purification of Retroinverse Peptides Incorporating Detectable Label Syntheses of peptides was performed using an Fmoc/tBu methodology optimized for amyloid sequences (El-Agnaf et al., (2000) BBRC, Vol. 273: pp 1003-07). HATU (2-(1H-7-Azabenzotriazol-1-yl)-1,1,3,3-tetramethyl uronium hexafluorophosphate) was used as coupling agent for Fmoc-protected amino acids on PEG-PS resin, and double coupling over the α-synuclein binding sequences was performed during the synthesis. A ε-Biotin-Lys tag was incorporated at the C-terminal end of the α-synuclein binding sequences to facilitate detection of the peptides in experimental systems. Poly D-arginine [$r_6$] or polyamines were incorporated at the C- or N-termini of the peptides as a membrane-permeable carrier to aid delivery into living cells and across the blood-brain barrier (BBB). [1,4,7,10-tetraazacyclododecane-1,4,7-tris(acetic acid-t-butyl ester)-10-acetic acid] (DOTA) was coupled to the N-terminus by double coupling using HATU. DOTA is incorporated for complexing gadolinium (Gd), which is a MRI contrast agent. The modified peptides were released and deprotected, and then purified on a preparative Phenomenix C4 column using reversed phase HPLC. Purity was confirmed by MALDI-TOF mass spectrometry (data not shown). Finally, the Gd salt of DOTA-peptides were prepared by incubation overnight with a 3-fold molar excess of Gd trichloride in water, and the pH was adjusted to 7.0.

The following peptides were produced:

```
(OR1)  Gd-DOTA-rGtvvaGK(biotin)-rrrrrr
(OR2)  Gd-DOTA-rGvvaGK(biotin)-rrrrrr
(OR3)  Gd-DOTA-rrrrrrGtvvaGK(biotin)-r
(OR4)  Gd-DOTA-rrrrrrGvvaGK(biotin)-r
(OR5)  Gd-DOTA-r-Sar-vva-Sar-K(biotin)-rrrrrr
(OR6)  Gd-DOTA-r-Sar-vva-Sar-K(biotin)-butadiamine
(OR7)  Gd-DOTA-r-Sar-vva-Sar-K(biotin)-pentadiamine
```

α-synuclein binding sequences are underlined. Lower case indicates D-configuration amino acids, i.e. this is the retroinverse sequence of the binding region of α-synuclein. Thus, for example, GtvvaG in OR1 corresponds to the sequence GAVVTG in wild-type α-synuclein (residues 68 to 73 of SEQ ID NO:1). Sarcosine (Sar) is incorporated in place of Gly in peptides OR5, 6 and 7. The sarcosine is N-methylglycine and adds to proteolytic resistance, solubility and blood-brain barrier (BBB) permeability.

Preparation of α-Synuclein:

Recombinant human α-synuclein was expressed in *Escherichia coli* and purified by FPLC as previously described by us (El-Agnaf, et al., 1998). The purity of α-synuclein protein was confirmed by HPLC, SDS-PAGE and mass spectroscopy.

Preparation of α-Synuclein Amyloid Fibrils:

Recombinant α-synuclein was dissolved in standard phosphate buffered saline, pH 7.4 (PBS) at 50 µM and incubated at 37° C. for up to 7 days in an Eppendorf Thermomixer with continuous mixing (1000 rpm). Amyloid fibril formation was monitored by Th-T binding assay and also confirmed by electron microscopy (data not shown).

Soluble aggregates of α-synuclein were produced by nitration or by treatment with dopamine. Nitration is performed as follows: 0.7 mg/ml lypholised α-synuclein are dissolved in 700 µl of water. 1% TNM in ethanol Nitration of α-synuclein was induced by adding a 50 µl aliquot of 1% tetranitromethane in ethanol to 500 µl of 1 mg/mL protein solution. The reaction mixture was stirred vigorously at room temperature for 10 min. The procedure was repeated with addition of another 50 µl aliquot of 1% TNM solution under the same conditions. After 10 min, urea was added to a final concentration of 2M and this protein mixture was dialyzed with four changes of appropriate buffer at pH 7.8 to completely remove unreacted TNM. The nitration of α-synuclein was confirmed by immunoblotting using specific monoclonal antibody to nitrated α-synuclein (data not shown).

Dopamine treatment is performed as follows: Dopamine and α-synuclein are mixed at a 1:1 ratio in water (typically 50 µM α-synuclein:50 µM Dopamine), then incubated at 37° C. for up to 8 days in an Eppendorf Thermomixer with continuous mixing (1400 rpm). The formation of α-synuclein oligomers was confirmed by western blotting and specific oligomeric-ELISA assay, whilst α-synuclein fibril formation was monitored by Th-T binding assay and confirmed by EM (data not shown).

EXAMPLE 2

Binding of Peptides to Coated α-Synuclein Aggregates

ELISA Assays

Various concentrations of fresh, or aggregated α-synuclein solutions (20-200 pmol/well) were coated on a microtiter plate to dry overnight at 37° C. Aggregated α-synuclein was therefore fixed to the microtiter plate. Aggregated α-synuclein was produced either by aging, dopamine treatment or nitration as indicated on the figures. After washing with PBS containing 0.05% Tween-20 (PBST) and blocking with blocking buffer (PBS containing 2.5% gelatin and 0.05% Tween-20), the biotinylated peptides (200 pmol/well in PBS) or BSA protein (negative control) were added and incubated for 1.5 hrs at room temperature (RT).

Binding of peptides to α-synuclein was quantified using enzyme-linked avidin. Briefly, the plates were washed three times with PBST before the addition of 100 µl/well of extravidin peroxidase diluted at 1:5,000 in blocking buffer. Plates were then washed three times with PBST before the addition of TMB peroxidase substrate. Plates were left for 15 minutes at RT for colour to develop. The reaction was stopped by addition 100 µl/well of 0.5M sulphuric acid and the plates were read at 450 nm in a spectrophotometer. All peptides showed concentration dependent binding to coated α-synuclein, whereas very low binding to coated BSA protein was observed for all peptides (FIG. 2). Peptides OR1&2 have showed high binding to both fresh and aggregated coated α-synuclein (FIG. 2A, B), whereas, under the same conditions, peptides OR3&4 showed more specific binding to the aggregated α-synuclein (FIG. 2C, D).

Figure 3B:
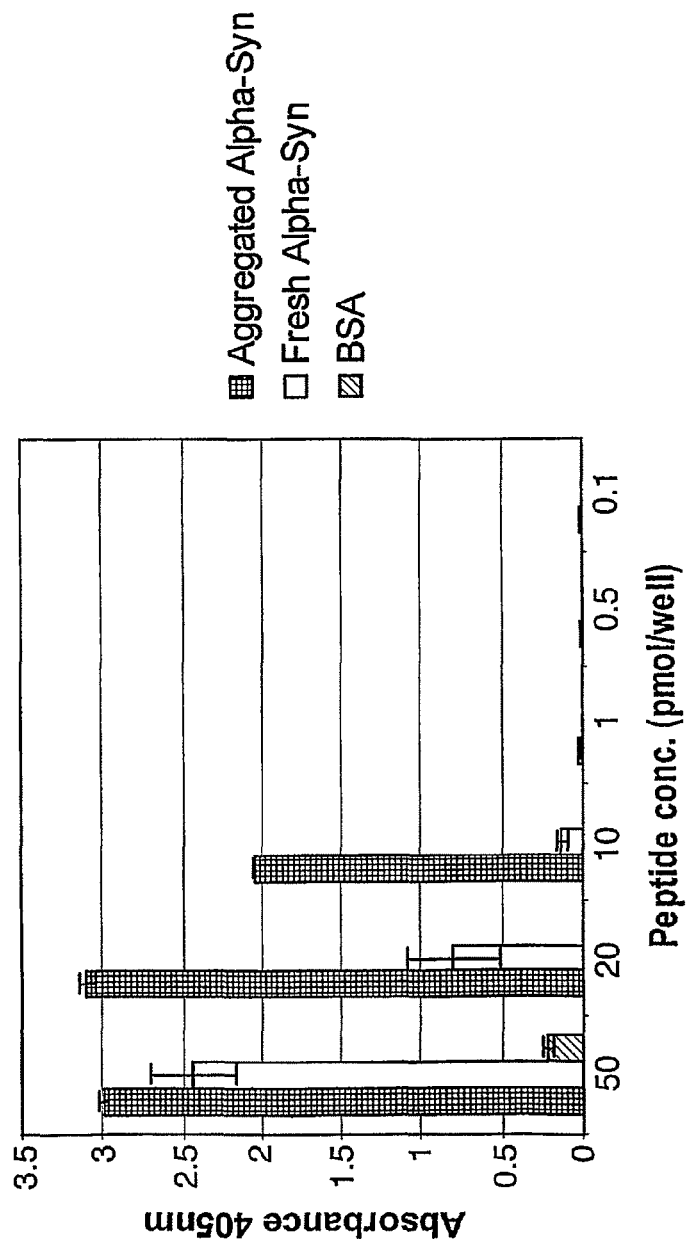
FIG. 3 A-E shows that peptides OR1 to 5 (respectively) of the invention bind more effectively to preformed α-synuclein aggregates than unaggregated, fresh α-synuclein at a range of peptide concentrations when the α-synuclein is coated on microtiter plates at 200 pmol/well and peptide solution is added to the wells.

The effect of peptide concentration on binding to a fixed concentration of α-synuclein was tested by coating microtiter plates as above with 100 or 200 pmol/well of α-synuclein. Peptides OR1&2 showed more binding to the aggregated than to the fresh α-synuclein at 100 pmol/well α-synuclein (FIG. 3A, B). The lowest binding concentration detected for both peptides was 10 pmol/well. Peptides OR3 to 5 showed highly specific binding to aggregated α-synuclein at 200 pmol/well α-synuclein (FIG. 3C, D, E). The lowest binding concentration detected for all three peptides was 10 pmol/well. The binding properties of peptides 6 & 7 to coated fresh or aged α-synuclein were also tested. The binding for peptides 6&7 was detectable when aggregated α-synuclein was coated at 500 pmol/well (data not shown).

Figure 5:
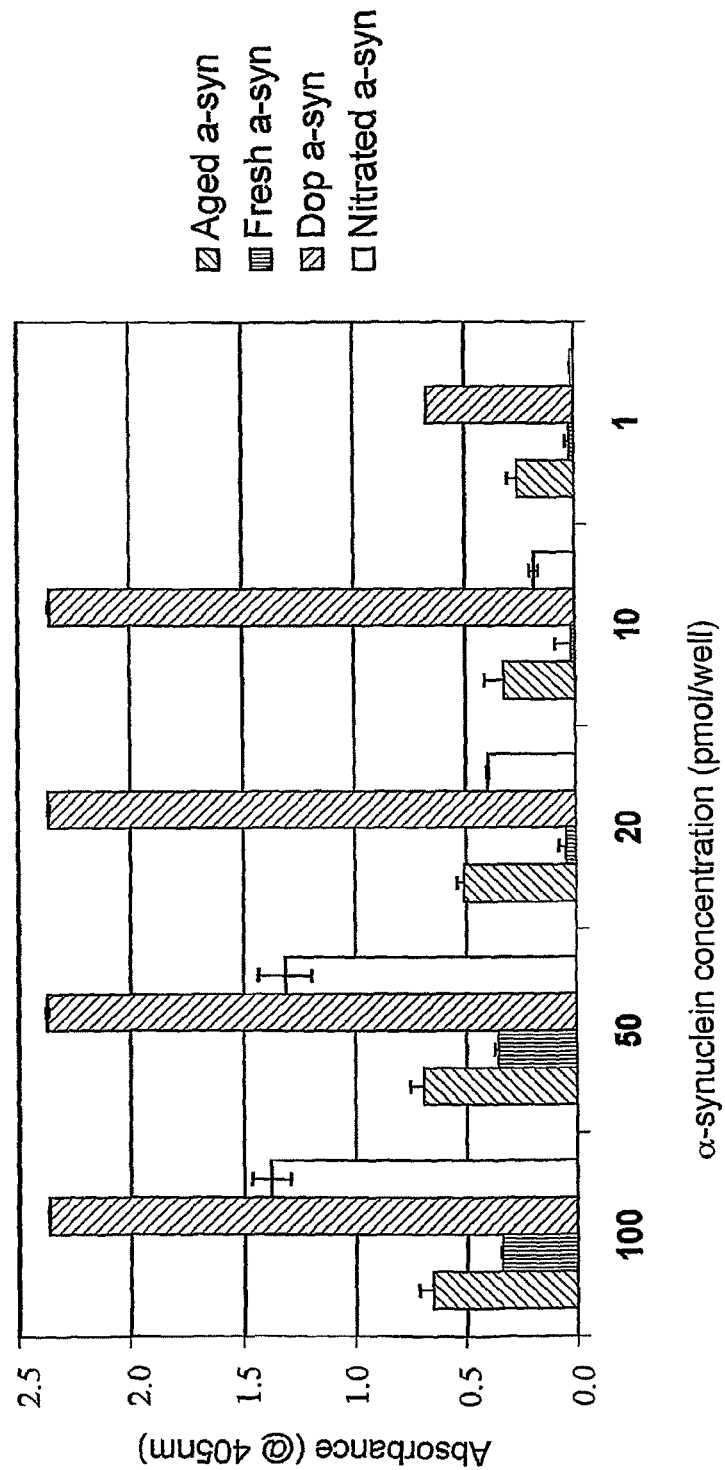
FIG. 5 shows that the peptides of the invention bind more effectively to preformed α-synuclein aggregates generated either by aging (insoluble aggregates), or by dopamine treatment or nitration (soluble aggregates) than unaggregated, fresh α-synuclein at a range of α-synuclein concentrations when the α-synuclein is coated on microtiter plates and peptide solution is added to the wells.

Peptide OR5 showed highly specific binding to all forms of aggregated α-synuclein (FIG. 5) with particularly high specificity for dopamine treated α-synuclein. The lowest binding concentration detected for dopamine treated α-synuclein was 1 pmol/well. Dopamine treated and nitrated α-synuclein are physiological approximations of the soluble aggregates (or adducts) present during the early stages of synucleinopathic diseases. Accordingly this data confirms that the peptides of the invention have properties suitable for the early detection and diagnosis of such diseases.

Figure 7:
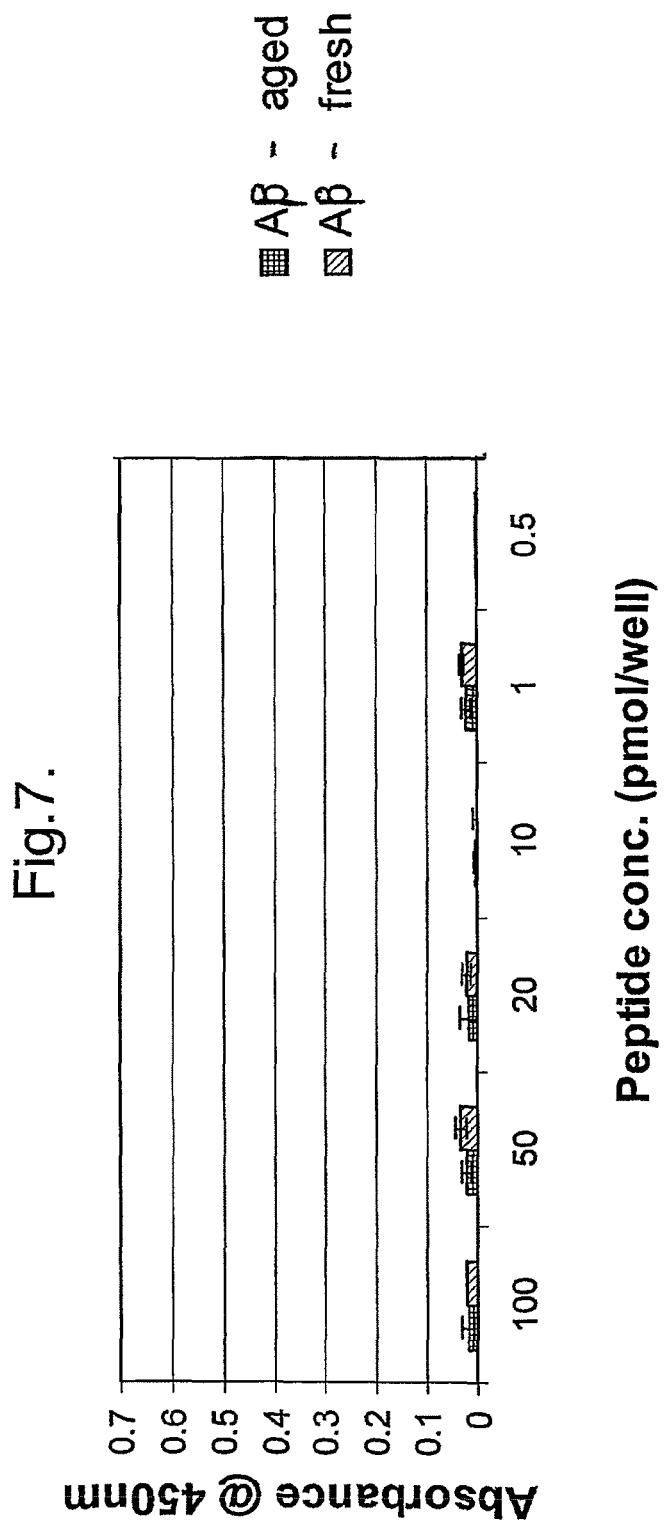
FIG. 7 shows that the peptides of the invention do not bind to the major component of protein aggregates in Alzheimer's disease (Aβ) in either aged, aggregated or fresh, unaggregated forms, at a range of peptide concentrations when the peptides are coated on microtiter plates and Aβ solution is added to the wells. Similar results were obtained for other polypeptide aggregates, such as British dementia peptide (ABri) (data not shown).

Control experiments coated microtiter plates with various concentrations of other proteins associated with amyloid fibril formation in neurodegenerative diseases, in particular the major component of protein aggregates in Alzheimer's disease (Aβ), the British dementia peptide (ABri). The peptides of the invention were demonstrated to have no affinity for Aβ (FIG. 7) or ABri (data not shown).

Immunogold Assays

Figure 6:
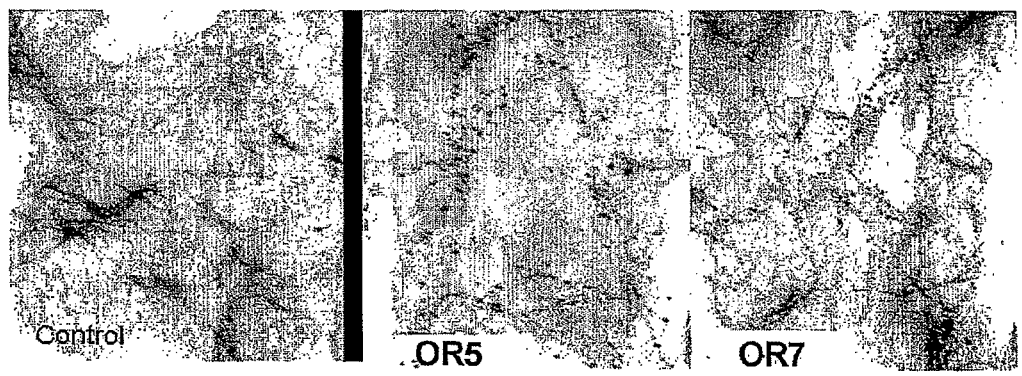
FIG. 6 EM micrographs show binding of the peptides of the invention (OR5 and OR7) to preformed aggregates (mature amyloid fibrils) of α-synuclein using the immunogold assay system.

Copper grids were placed on 50 µl of 50 µM aggregated α-synuclein for 1 hour and then washed on 50 µl of PBS for 2 minutes before being placed on 50 µl blocking buffer (Vector) for 1 hour 30 minutes. Grids were washed 5 times with PBS (5 minutes each) and then soaked in either 0.1 µm/ml peptide 5 (in blocking buffer) or blocking buffer only (negative control) for 1 hour 30 minutes at room temperature. Grids were then washed 5 times with PBS (5 minutes each) and soaked in 50 µl of streptavidin-gold label (1:50) in blocking buffer for 30 minutes at room temperature. Grids were again washed 5 times with PBS (5 minutes each) and soaked in 50 µl of uranyl acetate (2% in distilled water) for 1 minute at room temperature before viewing under a transmission electron microscope. The results indicate peptides OR5 and OR7 bind to preformed α-synuclein aggregates (FIG. 6). No gold signal was detected on the negative control grid indicating that there is no non-specific binding of streptavidin-gold label.

EXAMPLE 3

Binding of Coated Peptides to Free α-Synuclein Aggregates

Peptides (100 pmol/well) were coated on a microtiter plate to dry overnight at 37° C. The peptides were therefore fixed to the microtiter plate. After washing with PBS containing 0.05% Tween 20 (PBST) and blocking with blocking buffer (PBS containing 2.5% gelatin and 0.05% Tween 20), various concentrations (0.001-200 pmol/well) of fresh or aggregated α-synuclein solution (produced by aging), or BSA protein (negative control) were added and incubated for 1.5 hrs at RT. Binding of α-synuclein to peptides was quantified using enzyme-linked antibody specific for α-synuclein. Briefly, the plates were washed three times with PBST before addition of the polyclonal rabbit α-synuclein antibody FL-140 at 1:1000 (in PBS). Plates were then washed three times with PBST before the addition of TMB peroxidase substrate. Plates were left for 15 min at RT for colour to develop. The reaction was stopped by addition 100 µl/well of 0.5M sulphuric acid and the plates were read at 450 nm in a spectrophotometer.

Peptides OR4 (FIG. 4A) and 5 (FIG. 4B) captured more of the aggregated than the fresh α-synuclein. These results confirm that the peptides of the invention are more specific for α-synuclein fibrils than monomeric α-synuclein.

EXAMPLE 4

Ability of Peptides of Invention to Enter Living Neuronal Cells

SH-SY5Y or M17 neuroblastoma cells were grown in 15 ml medium in confluent flasks before splitting each suspension into petri dishes and allowing cells to grow on coverslips (~5×10³/plate) until the next day. Cells were then incubated with different peptides at 50 µM in growing media (total volume=2 ml). A peptide identical to peptide OR1 but lacking the poly D-arginine [$r_6$] was included as a control. After 15 min incubation with respective peptides, the cells were washed 3 times with PBS. 2 ml of fixing solution (4% paraformaldehyde in PBS) was added to the cells which were then incubated for 30 min at room temperature. Fixing buffer was removed and 2 ml of permeabilization buffer (0.2% Triton-X-100 in PBS) was added to the cells for 30 min at room temperature and then removed. 2 ml of Blocking buffer was added, left for 1 hour at RT and then removed before addition of 1:100 FITC [Avidin labelled Fluorescein] (Vector Labs) in blocking buffer. Cells were incubated for 1 hour and then washed twice with PBS 0.05% tween. The coverslips were removed and plated with the cell bearing surface downwards on a glass slide, with the addition of a drop of mounting medium (Dako Cytomation). Cells were then visualized under the confocal microscope.

Figure 8:
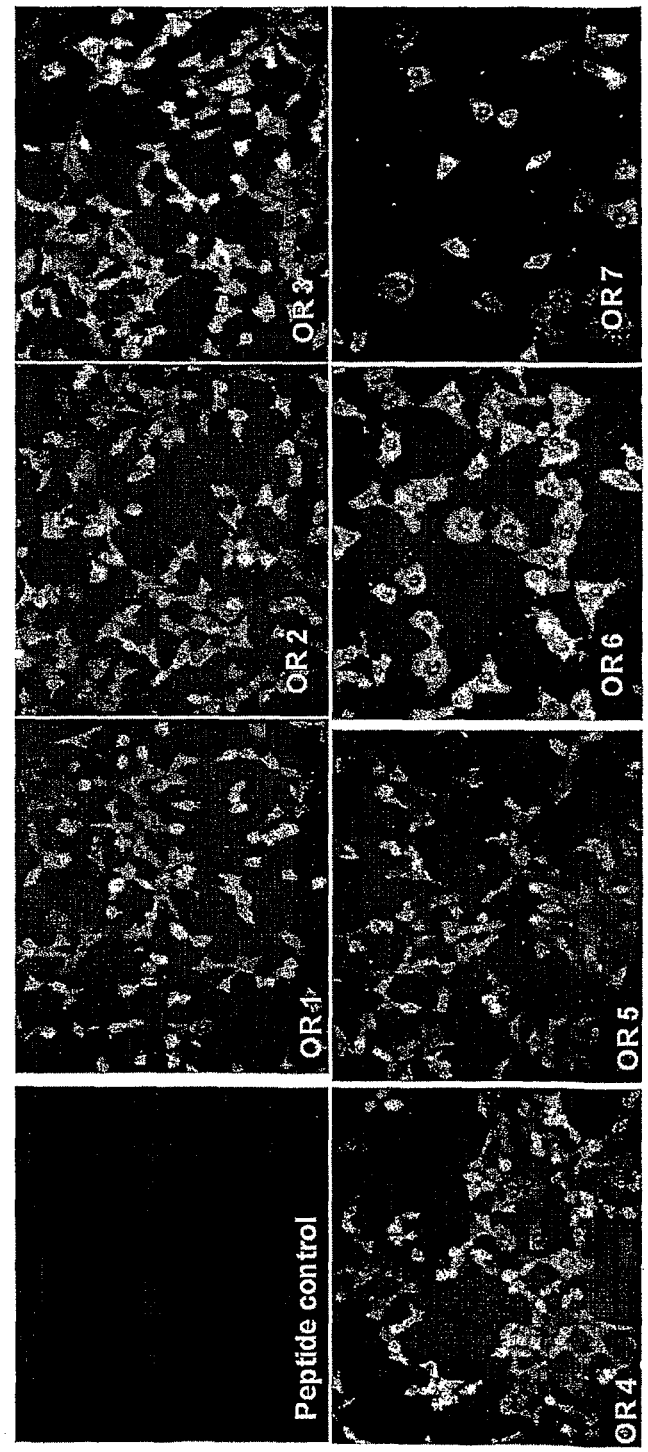
FIG. 8 shows that the peptides of the invention are taken up efficiently by the human neuroblastoma cells line SH-SYSY. Similar results were obtained for the human neuroblastoma cells line M17 (data not shown).

Fluorescent-labeled peptides of the invention were observed as a fluorescent signal in all living SH-SY5Y cells (FIG. 8), and were found to be distributed throughout the cells, whereas, cells treated with the control peptide showed no fluorescent signal in any living cells. Peptides 1 to 5 were observed as fluorescent signals in living cells after 30 minutes incubation; peptides 6 and 7 were observed in living cells after 2 and 4 hrs incubation respectively. Similar results were obtained for M17 cells (data not shown). Thus the peptides of the invention have the ability to cross cell membranes and enter living neuronal cells.

EXAMPLE 5

Cellular Clearance of Peptides

Figure 9:
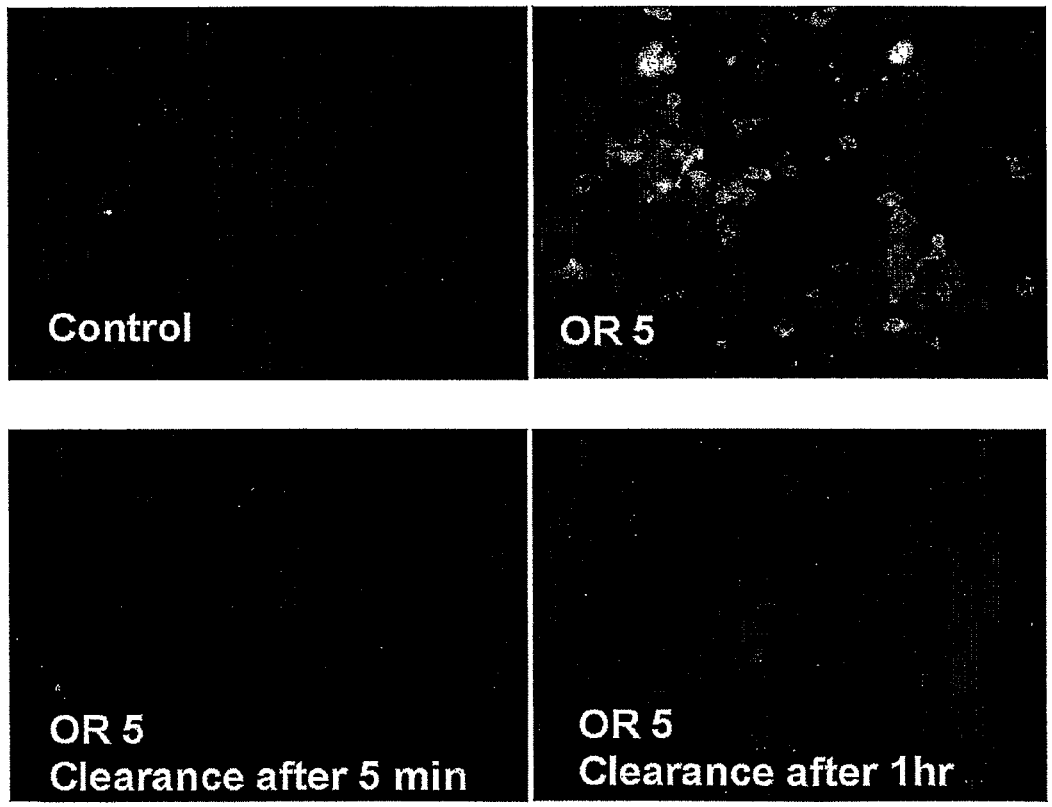
FIG. 9 shows peptide OR5 clearance from cells over time.

The ability of the cells to clear the peptides after they had entered the cells was tested. Cells were incubated with the peptides for 30 min at 37° C. to allow them to take up the peptides. The cell media was then replaced with fresh media without peptides and incubated for up to 24 hrs. The cells cleared the peptides as early as 5 min, and by 1 hr the cells have managed to clear the peptides completely (FIG. 9). Interestingly, after 4 hrs the cells have again shown some uptake of the peptides, which were cleared again by 24 hrs.

EXAMPLE 6

Evaluation of Cytotoxicity of Peptides of the Invention

The cytotoxicity of the peptides on human neuroblastoma cell line M17 has been assessed using a standard MTT assay. The MTT [3-(4,5-dimethylthiazol-2-yl)-2,5-diphenyltetrazolium bromide] assay, first described by Mosmann (J Immunol Methods. 1983; 65(1-2):p 55-63), is based on the ability of a mitochondrial dehydrogenase enzyme from viable cells to cleave the tetrazolium rings of the pale yellow MTT and form a dark blue formazan crystals which is largely impermeable to cell membranes, thus resulting in its accumulation within healthy cells. Solubilisation of the cells by the addition of a detergent results in the liberation of the crystals which are solubilised. The number of surviving cells is directly proportional to the level of the formazan product created. The color can is then quantified by simple colorimetric assay on a spectrophotometer.

Figure 10:
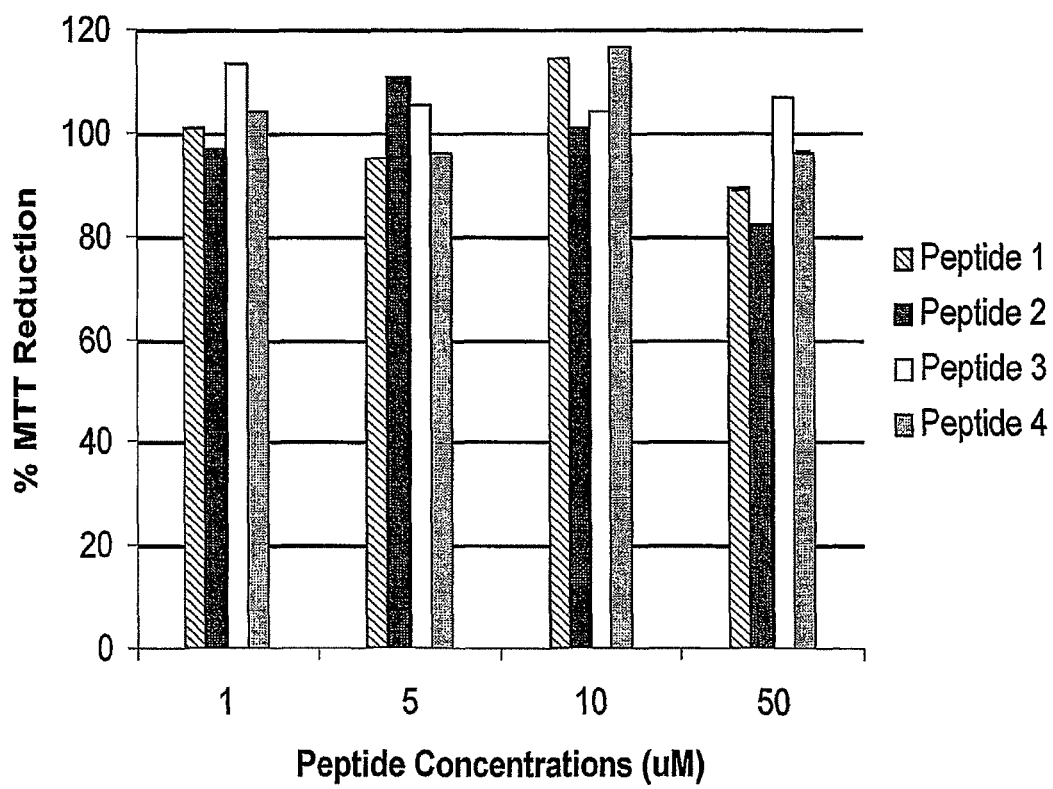
FIG. 10 shows that the peptides of the invention exhibit no cytotoxicity to human neuroblastoma cell lines.

As shown in FIG. 10, none of peptides OR1 to 4 exhibited any significant cytotoxicity towards M17 cells following treatment with 1-50 µM of the peptides for up to 48 hrs. Similar results were obtained with peptides OR5 to 7 (data not shown) and for all peptides with the human neuroblastoma SH-SY5Y cell line.

EXAMPLE 7

Figure 11:
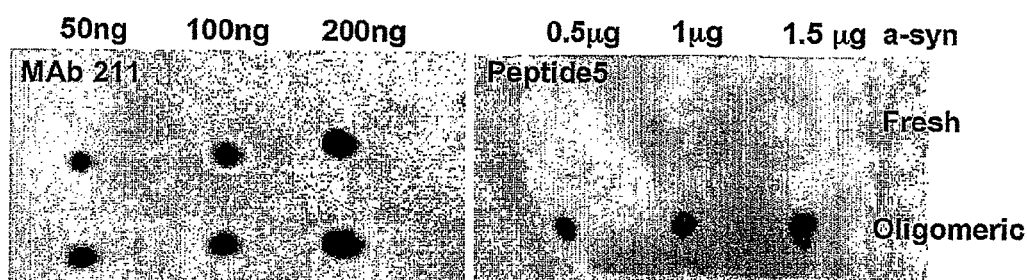
FIG. 11 shows dot blots demonstrating the binding of biotinylated-peptide OR5 to α-synuclein oligomers FIG. 12 demonstrates that Lewy Bodies (LBs) in the post-mortem brain are labelled by the peptide OR5 of the invention.

Confirming the Binding of Biotinylated-Peptides to α-Synuclein Amyloid Oligomers by Dot Blotting The binding of the peptides to the oligomeric α-synuclein was also tested using dot blotting. Monomeric α-synuclein (fresh α-synuclein solution) and oligomeric α-synuclein (dopamine treated α-synuclein) was spotted onto a nitrocellulose membrane. After the samples had been dried at room temperature for 2 hrs, the membranes were blocked, and then anti-α-synuclein MAb 211 or biotinylated-peptides were added to the membranes and incubated for 1.5 hr at room temperature. After gentle washing the membranes were treated with Extravidin-peroxidase or anti-mouse-peroxidase as appropriate. The binding of 211 and the peptides was detected using ECL reagents (Pierce). As shown in FIG. 11 the biotinylated-peptides bind specifically to the oligomeric but not monomeric forms of α-synuclein.

EXAMPLE 8

Investigating the Binding of the Peptides to Native α-Synuclein Aggregates in Brain

ELISA

Using an antibody specific to α-synuclein fibrils (anti-FILA—gift from Poul Jensen, University of Aarhus, Denmark), the inventor has developed an ELISA to quantify aggregates of native α-synuclein in human brain lysates. Frozen post-mortem brain samples of frontal cerebral cortex from control, AD and DLB patients were homogenized in lysis buffer consisting of a mild detergent and a cocktail of protease inhibitors. Samples were centrifuged and supernatants were collected. The total protein concentration in the samples was measured and then adjusted to 3 mg/ml prior to analysis by the ELISA. The brain samples were coated on a microtiter plate for overnight incubation at 37° C., and after washing followed by blocking, anti-FILA was added to the wells and incubated for 2 hrs. The binding of anti-FILA to α-synuclein aggregates in the brain samples was quantified by HRP-labeled anti-rabbit antibody. Anti-FILA gave a strong signal in most DLB samples and only very few samples of AD compared to those measured in control brain samples.

Peptides of the invention tested using this ELISA method will demonstrate their binding to the aggregates of native α-synuclein in human DLB brains.

Immunohiostochemistry

Binding of the peptides was investigated using 5 mm wax sections of formalin-fixed post-mortem PD and DLB brains, or cryostat sections of the fresh frozen brains. The sections were first immunostained with anti-α-synuclein antibody (MAb 211 or FL-140) as control and then compared under the microscope to successive sections incubated with the tested peptides, and peroxidase-avidin, to determine whether Lewy Bodies (LBs) in post-mortem brain are labelled by the peptides.

Figure 12A:

Brain sections were immersed in water and placed on slides, then incubated in xylene for 5 min. The xylene was exchanged, and slides incubated for a further 5 min, prior to quenching of endogenous peroxidase activity by incubation with 3% hydrogen peroxide in methanol at room temperature for 30 min. Slides were then washed with the following: 100% ethanol 5 min, 100% ethanol 5 min, 90% ethanol 5 min, 70% ethanol 5 min, formic acid 5 min, 70% ethanol 5 min, distilled water (3 changes) 5 min, PBS 5 min. The slides were incubated in blocking buffer (Vector Labs) for 90 min at 37° C., and washed in PBS for 5 min. Anti-α-synuclein antibody FL-140 was added in blocking buffer and incubated overnight at 4° C., prior to washing with PBS (3 changes over 5 min). Goat anti-rabbit-FITC (1:100 in blocking buffer) was then added and incubated for 1 hour at 37° C., prior to washing with PBS (3 changes over 5 min). Slides were then mounted for viewing under the fluorescence microscope; the F1-140 showed specific staining to the LBs (see FIG. 12A).

Figure 12B:
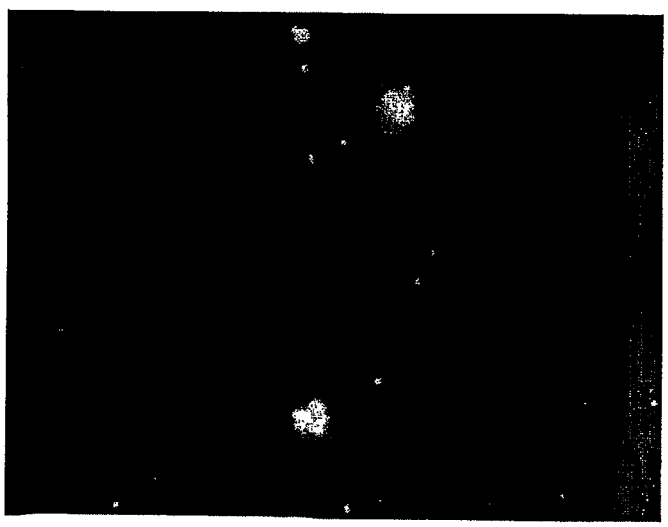

The binding of the peptides on 5 mm cryostat sections of fresh frozen post-mortem PD brains was then assessed. The slides were incubated in blocking buffer (Vector Labs) and washed in PBS. Peptide OR5 (0.05 mg/ml) was added in blocking buffer and incubated overnight at 4° C., prior to washing with PBS. Avidin-FITC (1:100 in blocking buffer) was then added and incubated for 1 hour at 37° C., prior to washing with PBS. Slides were then mounted and viewed under fluorescence microscope. Peptide OR5 showed specific staining to the LBs as shown in the FIG. 12B. The results demonstrate that OR 5 binds specifically to LBs in PD post-mortem brain sections.

EXAMPLE 9

Investigating the Binding of Biotinylated-OR Compounds to α-Synuclein Aggregates in Cell Models This example utilises the inducible TET-off regulated SH-SY5Y system from Dr. Kostas Vekrellis (Foundation For Biomedical Research Academy of Athens). These transfected cells have shown to produce both soluble and insoluble aggregates of α-synuclein. The binding of the OR compounds to α-synuclein aggregates was investigated in this cell model.

Cells expressing A53T were grown on coverslips in media without doxycycline and were differentiated for 7 days by adding retinoic acid at 10 µM. On day 6, cells were treated with 1 µM MG132 in media containing retinoic acid for 24 hrs. The biotinylated-OR5, 6 and 7 were added to the media at 5 µM for 1, 2 & 4 hrs respectively at 37° C.

The media for the cells was then changed with fresh media without peptides and then incubated for another 15 mins for the cells to clear up the unbound peptides to α-synuclein aggregates. The cells were fixed and then treated with 0.2% Triton X in PBS for 15 minutes at RT, and after washing with PBS the blocking buffer, 0.5% BSA, was added.

The cells were stained with anti-α-synuclein antibodies (MAb 211 or FL-140 (Santa Cruz Biotechnology)), and with Streptavidin-FITC (Sigma). α-synuclein aggregates were detected after staining with anti-mouse TRITC (Sigma) or anti-rabbit TRITC (Jackson ImmunoResearch Inc.) as appropriate.

The formation of α-synuclein aggregates was investigated in the differentiated cells using fluorescence microscopy. Both anti-α-synuclein antibodies showed dispersed staining of small aggregates of α-synuclein; few aggregates are formed in the perinuclear region (FIGS. 13A and 13B). However, in undifferentiated cells α-synuclein was diffusely distributed throughout the entire cytoplasm (data not shown). The staining of the biotinylated-OR compounds to α-synuclein aggregates in the cells was also investigated. The results indicate that peptides OR5, 6 and 7 bind to α-synuclein aggregates formed inside cells (FIGS. 13A and 13B). Interestingly, the aggregates of α-synuclein co-stained with α-synuclein antibody and the biotinylated-OR compounds. No signal was detected in the negative control cells (data not shown), indicating that there is no non-specific binding of streptavidin-FITC or anti-mouse TRITC and anti-rabbit TRITC to α-synuclein aggregates. The colocalization of the biotinylated-OR compounds with anti-α-synuclein antibody in the cells indicates their binding to the same aggregates of α-synuclein.

EXAMPLE 10

Microscopic Investigation of the Blood-Brain Barrier (BBB) Permeability and Pharmcokinetics of the Lead Compounds in Normal Mice Normal mice were injected intravenously with 100 µg/100 µl of peptide OR6 and 50 µg/200 µl of peptide 5 or PBS solution (n=2 for each group). Animals injected with OR6 were sacrificed after 5, 15, 30 and 60 min, whilst mice injected with OR5 were sacrificed after 5, 10, 15, 20 and 30 min. The whole brains, kidney and liver were removed. The tissues were fixed in 10% formaldehyde in phosphate buffer (PB) for over night at room temperature (RT) and next day were then transferred to 30% sucrose in PB and incubated for another over night at 4° C. The brains were then cut into 70-mm frozen sections using a cryostat. Brain slices were washed with PBS before incubated with 3% hydrogen peroxide (in 50% ethanol) for 30 min at RT. After washing with PBS, the sections were incubated with Extravidin peroxidase (1:500 in PBS containing 0.3% triton) and incubated for 1 hr at RT, prior to washing with PBS (2 changes over 5 min) and the last wash in PB. DAB (3,3' diaminobenzidine tetrahydrochloride) is applied for 15 min, before washing 3× in PB for 5 min. The sections were placed on gelatin coated slides and left to dry overnight. Next day the slides were hydrated in water for 3 min and then dehydrated for 5 min in each of: 50% ethanol, 70% ethanol, 95% ethanol, 100% ethanol (2×) and xylene (2×). Slides were then mounted in DPX-xylene for viewing under the microscope.

Peptide OR5

The pharmacokinetic results derived from the immunohistochemistry data imply that 5 mins after the mice were injected with OR5, a weak and diffuse pattern of staining was observed across the thalamus, the midbrain and the cerebellum. At 10 mins post-injection, staining had spread into the hippocampus, the pons as well as the thalamus. Also at this time the cerebellar staining was localized to the periphery of the cerebellum. 15 mins post-injection OR5 staining appeared in the brainstem including the midbrain and the pons, as well as the thalamus. Staining in these areas was maintained until 30 mins post-injection. Furthermore, at this time the staining in the cerebellum had spread across the entire cerebellar regions including its interior.

Peptides OR6 & OR7

The pharmacokinetic results for peptide OR6 suggests that the peptide crossed the BBB and stained quite strongly in the midbrain 5 mins post-injection. Weak but specific staining was also observed in the hypothalamus, thalamus and the periphery of the cerebellum both 5 and 15 mins after injection. Peptide 6 staining in the cerebellum reaches its peak 30 mins post-injection and stains all throughout the interior and the periphery of the cerebellum, similar to the cerebellar staining pattern observed for peptide 5. At 30 post-injection the staining in the thalamus and the midbrain becomes stronger and staining was also observed in the hippocampus. The staining in the hippocampus and midbrain seen at 30 mins post-injection is maintained at 1 hr after injection and additionally staining was observed in the hypothalamus. However, the staining in the cerebellum started to be fainter by this time, possibly due to the clearance of peptide 6 from this region. Similar results were obtained for peptide OR7.

Conclusion

All three peptides cross the BBB and during the course of time appear to localize to various regions of the brain. Peptide OR5 staining was observed in thalamus, midbrain, brain stem and hippocampus, whereas, OR6 and 7 preferentially stained in the hypothalamus while displaying stronger staining in the thalamus, midbrain, as well as the hippocampus. On the other hand, three peptides showed similar cerbellar staining patterns with time but by 1 hr post-injection peptide 6 might be getting cleared from the cerebellum, as suggested by the fainter staining observed. Previous experiments have also suggested that peptide OR5 might be getting cleared from the cerebellum after 1 hr. The stronger staining seen with OR6 and 7 can be attributed to the higher dose of the peptide injected into the mice.

EXAMPLE 11

MRI Investigation of the Blood-Brain Barrier (BBB) Permeability of the Lead Compounds Linked to the N-terminus of the lead compounds is Gadolinium (Gd), a paramagnetic contrast agent used in MRI imaging. Gd shortens T1, T2 and T2*. This results in a rise in the intensity of T1 weighted images and a decrease of T2/T2* weighted images.

To confirm that the compounds are linked to Gd, a tube containing water was compared with a tube containing a solution of a particular compound (at 82.2 µM) dissolved in water. For example, peptide OR7 gave a signal increase on a T1 weighted image as a result of the Gd content in the compound. Similar results were obtained for peptides OR5 and OR6.

Peptides OR5, 6 and 7 were then tested in normal C57BL6 control mice and wistar rat using MRI to investigate their BBB permeability and biodistribution in the brain.

Bolus Tracking (T2/T2*)

Gd, injected intravenously via a catheter, can be visualised by MRI during the first passage of a bolus of Gd through the brain as a signal decrease. If Gd leaks into the brain tissue a secondary signal increase is expected. The normal Gd dose given to rodents for bolus tracking experiments is 0.2 mmol Gd/kg. However, all experiments were carried out with low Gd concentrations (i.e. less than 0.2 mmol Gd/kg).

T1 Mapping

Figure 14A:
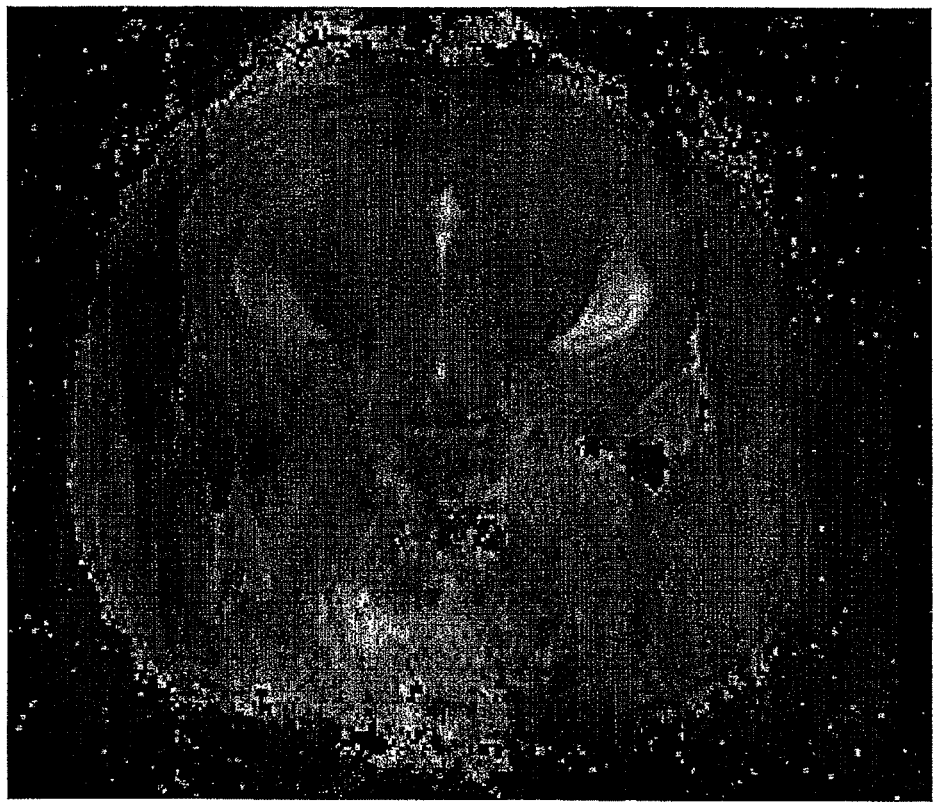
FIG. 14A shows an example of a T1 map.

T1 maps were created before and after intravenous injection. By comparing the T1 values in the maps it is possible to assess the distribution of the imaging compounds throughout the brain and the presence of Gd in certain regions. The recording time for a T1 map was 40 min. FIG. 14A shows an example of a T1 map. The T1 values are represented by different grey values. Two systems were used for the experiments: high field MRI systems from Bruker Biospin, a Pharmascan 70/16, and a BioSpec 94/20 USR with a magnetic field of respectively 7T and 9.4T. The animals were anaesthetized with the inhalation anaesthetic Isoflurane which was administered with a 1:2 gas mixture of $O_2$:$N_2$.

Post-processing of the data was done with Bruker ParaVision 4.0 imaging software, self-written Matlab routines and Amira 4.0 (Mercury computer systems, Inc.).

Peptide OR7

For in vivo MRI imaging, normal rats were injected intravenously with 2 mg of OR7 in 0.1 ml PBS to give 0.0012 mmol of Gd (more than 40 times lower than the normally used Gd concentration).

Figure 14B:
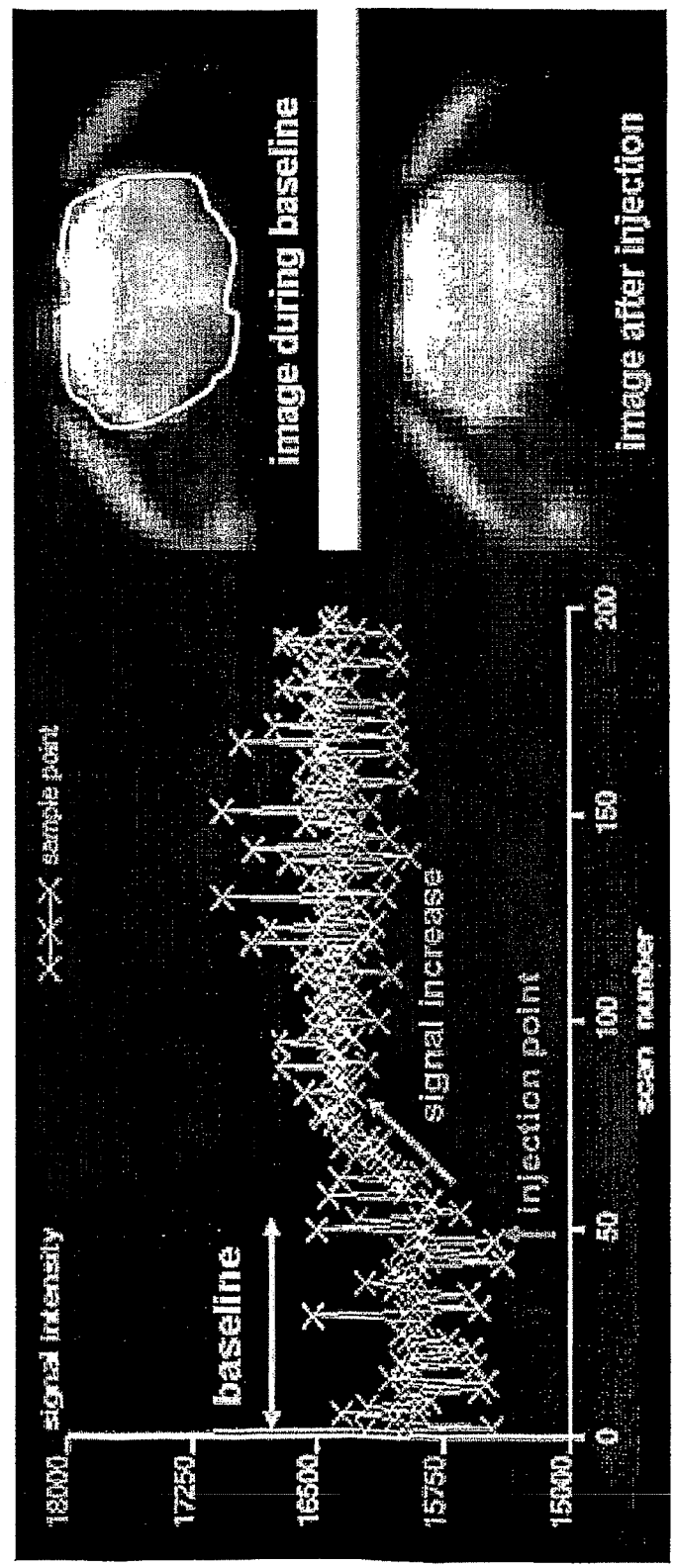
FIG. 14B shows MRI imaging of the brain after iv injection of peptide OR7.

After bolus injection of the compound the first passage was not observed, probably due to the low volume and/or concentration, but a signal increase was detected that demonstrated that OR7 has crossed the BBB. FIG. 14B represents the region of interest shown to the right of the graph (the whole brain); the same time profile was also seen for smaller regions.

For the bolus tracking experiment specific positions in the brain were selected since only a single slice mode is possible. This limited the spatial information of what was happening in the other regions. After this bolus multi-slice anatomical images (T2 weighted) were taken to detect more focal leakage of Gd. From those images Gd spots were not seen (due to lower intensity).

The bolus tracking data clearly suggests retention of OR7 in the brain after injection of a high dosage containing (0.0012 mmolGd and 2 mg peptide) in a rat.

Peptide OR6

In this experiment T1 mapping but not bolus tracking was performed. T1 was measured prior to the injection, and the mouse was removed from the magnet. The mouse was then injected with OR6 solution (0.3 mg containing 0.18 µmmol Gd) dissolved in 0.15 ml saline; the solution was injected slowly directly into the vein without the use of a long distance catheter (for this a smaller volume is needed). The mouse was put back in the magnet and T1 was measured again.

In the table shown below the mean T1 values are presented for 3 regions in the brain: Caudate Putamen (CPu), Hippocampus (Hippo), and Deep Mesenchephalic nucleus (DpMe). The caudate putamen was segmented because it is a large region in the front of the brain; the hippocampus is an important region that is located next to the ventricles.

In Table 2, T1 values for the tested mouse are presented. B=before injection, A=15 min after injection (the duration of the recording is 40 min), and A3d=3 days after the injection. The T1 values decreased significantly in all regions following the injection with OR6 solution, and after 3 days the signals recovered to normal.

TABLE 2

| | OR 6 | | |
|---|---|---|---|
| | B | A | A3d |
| CPu | 1747 | 1008 | 1705 |
| Hippo | 1771 | 1045 | 1752 |
| DpMe | 1630 | 940 | 1532 |

Peptide OR5

Two mice were injected with 0.20 ml and 0.15 ml of OR5 solution at 0.4 mg/ml containing 0.165 µmol and 0.124 µmol of Gd respectively. In the first mouse a first passage was visible after injection as well as an increase of the signal afterwards, which meant that when the OR5 was injected it had crossed the BBB.

The second mouse was also assessed and created a T1 map as had been done for OR6.

Table 3 presents the T1 values for the 2nd mouse. (B=before injection, A=15 min after injection (the duration of the recording was 40 min)). After the injection there was a slight decrease of the T1 values in the three segmented regions which suggests Gd is retained in those areas. The decrease in the signal was very small which is consistent with the small amount of Gd that was administered.

TABLE 3

| | A | B |
|---|---|---|
| CPu | 1930 | 1894 |
| Hippo | 1979 | 1923 |
| DpMe | 1612 | 1599 |

The experiment was repeated for OR5 with a lower concentration. A solution comprising 0.5 mg/ml of OR5 was injected into a third mouse with 0.30 ml (0.150 mg of OR5 and 0.0618 µmol of Gd), and a fourth mouse was injected with 0.1 ml solution (0.050 mg of peptide 5 and 0.0206 µmol of Gd). The results are shown in Table 4. For mouse 4, two successive T1 maps were recorded after the injections to look at the evolution of T1 values in time. The recording of the second map (A2) was started 55 min after injection.

TABLE 4

| | # mice | | | | |
|---|---|---|---|---|---|
| | 3 | | 4 | | |
| | B | A | B | A1 | A2 |
| CPu | 1694 | 1673 | 1640 | 1627 | 1633 |
| Hippo | 1783 | 1759 | 1787 | 1786 | 1781 |
| DpMe | 1514 | 1462 | 1457 | 1460 | 1479 |

The invention claimed is:

1. An agent comprising:
   i) a peptide of three to six amino acids comprising the amino acid sequence DThr-DVal-DVal-DAla or DVal-DVal-DAla;
   ii) a poly-D-Arginine, a polyamine or polyguanidine linked to the N— or C—terminus of the peptide (i) by a hydrophilic residue; and
   iii) (a) a detectable label selected from a radiolabel, a fluorescent label, or a magnetic contrast agent; or
      (b) a low molecular weight chelate selected from 1,4,7,10-tetraazacyclododecane-1,4,7-tris(acetic acid-t-butyl ester)-10-acetic acid (DOTA) or diethylene triamine pentaacetic acid (DTPA).

2. An agent according to claim 1, wherein said low molecular weight chelate is DOTA.

3. An agent according to claim 1 represented by any one of formulae (I) to (VIII):
   (I) DOTA-DArg-Nmethylglycine-DVal-DVal-DAla-Nmethylglycine-poly-D-Arginine[$r_6$]
   (II) DOTA-DArg-Nmethylglycine-DThr-DVal-DVal-DAla Nmethylglycine-poly-D-Arginine[$r_6$]
   (III) DOTA-DArg-Glycine-DVal-DVal-DAla-Glycine-poly-D-Arginine[$r_6$]
   (IV) DOTA-DArg-Glycine-DThr-DVal-DVal-DAla-Glycine-poly-D-Arginine[$r_6$]
   (V) DOTA- poly-D-Arginine[$r_6$]-Glycine-DVal-DVal-DAla-Glycine-DArg
   (VI) DOTA- poly-D-Arginine[$r_6$]-Glycine-DThr-DVal-DVal-DAla-Glycine-DArg
   (VII) DOTA-DArg-Nmethylglycine-DVal-DVal-DAla-N-methylglycine-butadiamine
   (VIII) DOTA-DArg-Nmethylglycine-DVal-DVal-DAla-N-methylglycine-Pentadiamine.

4. An agent according to claim 1 further comprising gadolinium.

5. An agent according to claim 1 further comprising a membrane-permeable carrier peptide selected from HIV-1 Tat-(48-60), flock house virus (FHV) coat-(35-49), Drosophila Antennapedia-(43-58), or polyamines.

6. An agent according to claim 1 wherein said hydrophilic residue is Glycine or N-methylglycine.

* * * * *

SEQUENCE LISTING

```
<160> NUMBER OF SEQ ID NOS: 7

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60
```

-continued

```
Asn Val Gly Gly Ala Val Val Thr Gly Val Thr Ala Val Ala Gln Lys
 65                  70                  75                  80

Thr Val Glu Gly Ala Gly Ser Ile Ala Ala Thr Gly Phe Val Lys
                 85                  90                  95

Lys Asp Gln Leu Gly Lys Asn Glu Gly Ala Pro Gln Glu Gly Ile
                100                 105                 110

Leu Glu Asp Met Pro Val Asp Pro Asp Asn Glu Ala Tyr Glu Met Pro
                115                 120                 125

Ser Glu Glu Gly Tyr Gln Asp Tyr Glu Pro Glu Ala
            130                 135                 140

<210> SEQ ID NO 2
<211> LENGTH: 35
<212> TYPE: PRT
<213> ORGANISM: Homo sapiens

<400> SEQUENCE: 2

Glu Gln Val Thr Asn Val Gly Gly Ala Val Val Thr Gly Val Thr Ala
 1               5                  10                  15

Val Ala Gln Lys Thr Val Glu Gly Ala Gly Ser Ile Ala Ala Ala Thr
                20                  25                  30

Gly Phe Val
        35

<210> SEQ ID NO 3
<211> LENGTH: 7
<212> TYPE: PRT
<213> ORGANISM: Homo sapiens

<400> SEQUENCE: 3

Gly Gly Ala Val Val Thr Gly
 1               5

<210> SEQ ID NO 4
<211> LENGTH: 4
<212> TYPE: PRT
<213> ORGANISM: Homo sapiens

<400> SEQUENCE: 4

Gly Ala Val Val
 1

<210> SEQ ID NO 5
<211> LENGTH: 5
<212> TYPE: PRT
<213> ORGANISM: Homo sapiens

<400> SEQUENCE: 5

Ala Val Val Thr Gly
 1               5

<210> SEQ ID NO 6
<211> LENGTH: 4
<212> TYPE: PRT
<213> ORGANISM: Homo sapiens

<400> SEQUENCE: 6

Val Val Thr Gly
 1
```

```
<210> SEQ ID NO 7
<211> LENGTH: 3
<212> TYPE: PRT
<213> ORGANISM: Homo sapiens

<400> SEQUENCE: 7

Val Thr Gly
1
```